(12) United States Patent
Kiesel et al.

(10) Patent No.: US 8,040,526 B2
(45) Date of Patent: Oct. 18, 2011

(54) IMPLANTING OPTICAL CAVITY STRUCTURES

(75) Inventors: Peter Kiesel, Palo Alto, CA (US); Oliver Schmidt, Palo Alto, CA (US); Michael Bassler, Menlo Park, CA (US); Richard H. Bruce, Los Altos, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 12/968,115

(22) Filed: Dec. 14, 2010

(65) Prior Publication Data
US 2011/0082353 A1 Apr. 7, 2011

Related U.S. Application Data

(62) Division of application No. 11/702,329, filed on Feb. 5, 2007, now Pat. No. 7,852,490.

(51) Int. Cl.
*G01B 9/02* (2006.01)
(52) U.S. Cl. ........................... 356/519; 600/310
(58) Field of Classification Search .................. 356/480, 356/481, 517, 519; 600/310, 316, 327, 325, 600/339, 341
See application file for complete search history.

(56) References Cited

U.S. PATENT DOCUMENTS

| | | | |
|---|---|---|---|
| 3,228,246 A * | 1/1966 | Rosenthal | 356/517 |
| 3,915,573 A * | 10/1975 | Knoll et al. | 356/454 |
| 4,417,815 A * | 11/1983 | Murray et al. | 356/480 |
| 4,873,989 A * | 10/1989 | Einzig | 600/505 |
| 5,144,498 A | 9/1992 | Vincent | |
| 5,151,585 A | 9/1992 | Siebert | |
| 5,168,325 A * | 12/1992 | Yoder-Short | 356/517 |
| 5,243,614 A | 9/1993 | Wakata et al. | |
| 5,394,244 A | 2/1995 | Tsai | |
| 5,414,508 A | 5/1995 | Takahashi et al. | |
| 5,422,714 A * | 6/1995 | Fladd | 356/128 |
| 5,461,477 A | 10/1995 | Marinelli et al. | |
| 5,784,507 A | 7/1998 | Holm-Kennedy et al. | |

(Continued)

FOREIGN PATENT DOCUMENTS
DE 19540456 5/1997
(Continued)

OTHER PUBLICATIONS

Kondziela, Accurately Measure Laser Spectral Characteristics, 2006, p. 1.

(Continued)

*Primary Examiner* — Hwa Lee
(74) *Attorney, Agent, or Firm* — Hollingsworth & Funk, LLC

(57) ABSTRACT

An implantable product includes an optical cavity structure with first and second parts, each of which can operate as an optical cavity. The first part includes a container with at least one opening through which bodily fluid can transfer between the container's interior and exterior when the product is implanted in a body. The second part includes a container that is closed and contains a reference fluid. The implantable product can also include one or both of a light source component and a photosensing component. Photosensed quantities from the first part's output light can be adjusted based on photosensed quantities from the second part's output light. Both parts can have their light interface surfaces aligned so that they both receive input light from a light source component and both provide output light to a photosensing component.

23 Claims, 10 Drawing Sheets

U.S. PATENT DOCUMENTS

| | | | |
|---|---|---|---|
| 5,793,485 A | 8/1998 | Gourley | |
| 5,945,676 A | 8/1999 | Khalil et al. | |
| 6,040,578 A | 3/2000 | Malin et al. | |
| 6,049,727 A | 4/2000 | Crothall | |
| 6,108,463 A | 8/2000 | Herron et al. | |
| 6,122,536 A | 9/2000 | Sun et al. | |
| 6,187,592 B1 | 2/2001 | Gourley | |
| 6,216,022 B1* | 4/2001 | Tyrrell et al. | 600/310 |
| 6,285,504 B1 | 9/2001 | Diemeer | |
| 6,295,130 B1 | 9/2001 | Sun et al. | |
| 6,429,022 B1 | 8/2002 | Kunz et al. | |
| 6,438,397 B1 | 8/2002 | Bosquet et al. | |
| 6,483,959 B1 | 11/2002 | Singh et al. | |
| 6,490,034 B1 | 12/2002 | Woias et al. | |
| 6,561,978 B1 | 5/2003 | Conn et al. | |
| 6,580,507 B2 | 6/2003 | Fry et al. | |
| 6,597,461 B1 | 7/2003 | Verma et al. | |
| 6,639,679 B2 | 10/2003 | Frojdh | |
| 6,694,158 B2 | 2/2004 | Polak | |
| 6,867,868 B1 | 3/2005 | Barbarossa | |
| 6,934,435 B2 | 8/2005 | Kane | |
| 6,952,603 B2 | 10/2005 | Gerber et al. | |
| 6,983,176 B2 | 1/2006 | Gardner et al. | |
| 7,011,630 B2 | 3/2006 | Desai et al. | |
| 7,012,696 B2 | 3/2006 | Orr et al. | |
| 7,024,236 B2 | 4/2006 | Ford et al. | |
| 7,027,848 B2 | 4/2006 | Robinson et al. | |
| 7,064,836 B2 | 6/2006 | Bechtel et al. | |
| 7,130,321 B2 | 10/2006 | Spinelli et al. | |
| 7,136,689 B2 | 11/2006 | Shults et al. | |
| 7,149,396 B2 | 12/2006 | Schmidt et al. | |
| 7,195,465 B2 | 3/2007 | Kane et al. | |
| 7,196,796 B2 | 3/2007 | Moriya et al. | |
| 7,256,888 B2 | 8/2007 | Staehr et al. | |
| 7,259,856 B2 | 8/2007 | Kachanov et al. | |
| 7,291,824 B2 | 11/2007 | Kiesel et al. | |
| 7,310,153 B2 | 12/2007 | Kiesel et al. | |
| 7,315,667 B2 | 1/2008 | Schmidt et al. | |
| 7,358,476 B2 | 4/2008 | Kiesel et al. | |
| 7,391,517 B2 | 6/2008 | Tebbia et al. | |
| 7,400,399 B2 | 7/2008 | Wawro et al. | |
| 7,420,677 B2 | 9/2008 | Schmidt et al. | |
| 7,433,552 B2 | 10/2008 | Kiesel et al. | |
| 7,466,409 B2 | 12/2008 | Scherer et al. | |
| 7,471,399 B2 | 12/2008 | Kiesel et al. | |
| 7,502,123 B2 | 3/2009 | Kiesel et al. | |
| 7,521,769 B2 | 4/2009 | Cunningham | |
| 7,522,786 B2 | 4/2009 | Kiesel et al. | |
| 7,524,459 B2 | 4/2009 | Adams et al. | |
| 7,545,513 B2 | 6/2009 | Kiesel et al. | |
| 7,547,904 B2 | 6/2009 | Schmidt et al. | |
| 7,554,673 B2 | 6/2009 | Kiesel et al. | |
| 7,633,629 B2 | 12/2009 | Kiesel et al. | |
| 7,695,680 B2 | 4/2010 | Unlu et al. | |
| 7,701,590 B2 | 4/2010 | Kiesel et al. | |
| 7,811,438 B2 | 10/2010 | Lean et al. | |
| 7,817,276 B2 | 10/2010 | Kiesel et al. | |
| 7,817,281 B2 | 10/2010 | Kiesel et al. | |
| 2003/0112443 A1* | 6/2003 | Hjelme et al. | 356/480 |
| 2004/0175734 A1 | 9/2004 | Stahler et al. | |
| 2005/0158868 A1* | 7/2005 | Trebbia et al. | 436/164 |
| 2008/0013092 A1 | 1/2008 | Maltezos et al. | |
| 2008/0186494 A1 | 8/2008 | Kiesel et al. | |
| 2009/0156917 A1 | 6/2009 | Martini et al. | |
| 2009/0220189 A1 | 9/2009 | Kiesel et al. | |

FOREIGN PATENT DOCUMENTS

| | | |
|---|---|---|
| WO | WO0201202 | 1/2002 |
| WO | WO2006133360 | 12/2006 |
| WO | WO2009015723 | 2/2009 |

OTHER PUBLICATIONS

McNichols et al., Optical Glucose Sensing in Biological fluids, an overview, p. 1.

Vogel, Tuneable Liquid Crystad Fabry=Perot Filters, 2002, p. 1.

File History for U.S. Appl. No. 11/702,329 on Dec. 14, 2010, 1477 pages.

File History for U.S. Appl. No. 10/922,870 on Dec. 14, 2010, 287 pages.

File History for U.S. Appl. No. 11/316,303 on Dec. 14, 2010, 536 pages.

File History for U.S. Appl. No. 11/633,302 on Dec. 14, 2010, 278 pages.

File History for U.S. Appl. No. 11/702,250 on Dec. 14, 2010, 202 pages.

File History for U.S. Appl. No. 11/702,363 on Dec. 14, 2010, 425 pages.

File History for U.S. Appl. No. 11/702,249 on Dec. 14, 2010, 323 pages.

File History for U.S. Appl. No. 11/702,325 on Dec. 14, 2010, 4287 pages.

File History for U.S. Appl. No. 11/702,321 on Dec. 14, 2010, 336 pages.

File History for U.S. Appl. No. 11/702,320 on Dec. 14, 2010, 579 pages.

File History for EP Application No. 08151021.6 retrieved from the European Patent Office Electronic File System on Mar. 22, 2011, 204 pages.

* cited by examiner

IMPLANTING OPTICAL CAVITY STRUCTURES

RELATED PATENT APPLICATIONS

This application is a divisional of U.S. patent application Ser. No. 11/702,329 filed Feb. 5, 2007, to issue as U.S. Pat. No. 7,852,490 on Dec. 14, 2010, which is incorporated herein by reference in its entirety.

This application is related to the following co-pending applications, each of which is hereby incorporated by reference in its entirety: U.S. Pat. Nos. 7,310,153; 7,433,552; 7,701,590; 7,471,399; 7,545,513; 7,502,123; U.S. Patent Publication No. 2008/0186494; U.S. Pat. Nos. 7,633,629; and 7,817,281.

BACKGROUND OF THE INVENTION

The present invention relates generally to techniques involving implantation of products in bodies, such as products that that include optical components and can be used to obtain information, such as about analytes.

U.S. Pat. No. 6,216,022 describes an implantable optical measurement device or system that has an entry window, an exit window, a reference path between the windows, and a measurement path between the windows. The reference path includes a reference element with known optical characteristics, and the measurement path is in fluid communication with the body fluids of a person. A first optical signal is directed through the person's tissue, the entry window, the reference path, the exit window, and again the person's tissue to an external optical sensor, and a second optical signal is directed through the same tissue, the entry window, the measurement path, the exit window, and again the same tissue to the external optical sensor. The first optical signal can be used to compensate for absorption, scattering, and other optical effects of the tissue on the second optical signal.

It would be advantageous to have improved techniques for implantable products, including improved techniques for products that include optical components.

SUMMARY OF THE INVENTION

The invention provides various exemplary embodiments, including products, systems, methods, apparatus, and devices. In general, the embodiments involve implantable products that include optical cavity structures.

These and other features and advantages of exemplary embodiments of the invention are described below with reference to the accompanying drawings.

DETAILED DESCRIPTION

Figure 1:
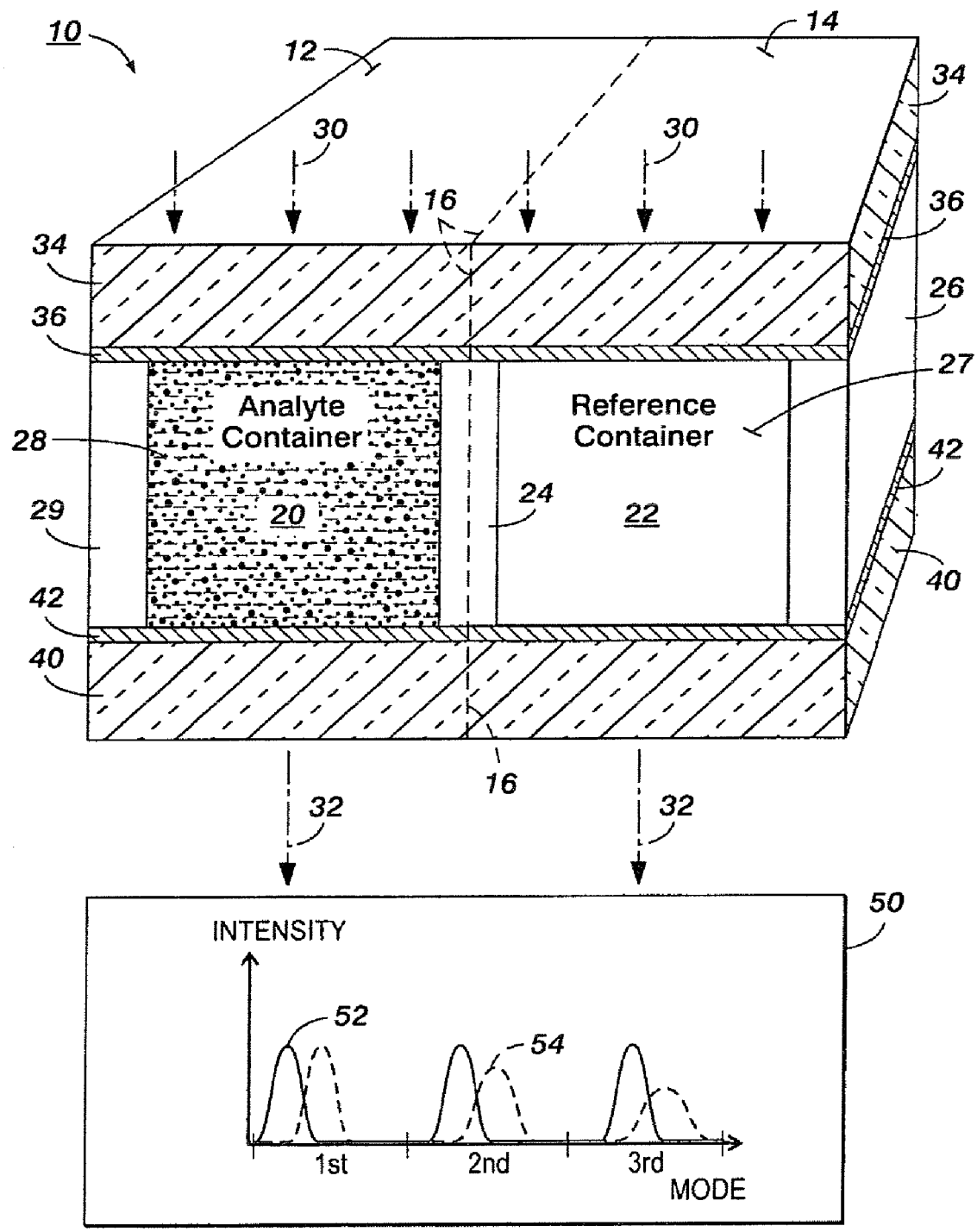
FIG. 1 is a schematic perspective diagram of a product that includes an optical cavity structure and that can be implanted in a body.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum.

The various exemplary implementations described below address problems that arise in using light to obtain information, such as about analytes in bodily fluids. One problem is that accurate information may be difficult to obtain because of various types of noise that may be present when light passes through a body. Where a small implanted product is used, another problem is the difficulty of obtaining sufficient interaction between light and analyte. A further problem with such products is that frequent calibration is typically required, such as with a non-optical test; in the case of optical glucose sensing, for example, frequent calibration using the standard blood test method is typically required—there is currently no solution allowing for continuous around-the-clock glucose level monitoring without regular use of the standard blood test for recalibration, such as every couple of hours.

Although the exemplary implementations described below can be used to obtain information about analytes in human bodies, the term "body" is used herein to refer to any living body or a part of such a body that includes fluids, and can include non-human or even non-animal bodies. Fluids that occur in bodies are referred to as "bodily fluids"; common examples of human bodily fluids include blood, lymph, and interstitial fluids, but there are many others.

As used herein, "to implant" a thing in a body refers to any operation that begins with the thing outside the body and ends with the thing at least partially inside the body. An "implantable product" is therefore any article of manufacture capable of being implanted in a body.

The term "photon" refers herein to a quantum of light, and the term "photon energy" refers herein to the energy of a photon. Light can be described as having a "photon energy distribution", meaning the combination of photon energies that are included in the light; highly monochromatic light, for example, has a photon energy distribution with one peak energy value. A photon energy distribution can be specified in space and time: For example, a photon energy distribution can be specified as a function of position, such as on a surface, or as a function of time; a photon energy distribution that is "homogeneous" is substantially the same at all relevant positions, such as the positions of a surface, while a photon energy distribution that is "stable" is substantially the same at all relevant times.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, light emitting diodes (LEDs), superluminescent LEDs (SLEDs), resonant cavity LEDs, sources of broadband light that is spectrally filtered such as with a monochromator, and so forth. A "tunable light source" is a light source that provides light with a predominant photon energy that can be changed in response to a signal or operation of some kind.

The term "laser" is used herein to mean any region, element, component, or device in which transitions between energy levels can be stimulated to cause emission of coherent light, such as in the ultraviolet, visible, or infrared regions of the spectrum. A "laser structure" is any structure that includes one or more lasers. A "laser cavity" is a region of a laser in which transitions can be stimulated to cause emission.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where light changes direction in a way that can be illustrated as a vertex between an incoming ray and an outgoing ray, the change may be referred to as a "reflection"; similarly, to "reflect" light is to cause the light to change its direction of propagation approximately at a surface, referred to herein as a "reflection surface". Where light propagates at less than c, it may be useful to obtain an "optical distance" of propagation; for any segment of length d in which speed of propagation is constant $\epsilon*c$, where $\epsilon \leq 1$, optical distance $D(\epsilon)=d/\epsilon$. An optical distance may be referred to herein as an "optical thickness", such as where light is propagating through a thickness of material.

To "photosense" is to sense photons, and to "photosense quantity" of photons is to obtain information indicating a quantity of the photons. Photons that are photosensed are sometimes referred to herein as "incident photons". A surface at which photosensing occurs is referred to herein as a "photosensitive surface".

A "photosensor" is used herein to refer generally to any element or combination of elements that senses photons, whether by photosensing quantity or any other information about the photons. A photosensor could, for example, provide an electrical signal or other signal that indicates results of sensing, such as a signal indicating quantity of incident photons; in general, signals from a photosensor that indicate results of sensing are referred to herein as "sensing results". If electrical sensing events occur in a photosensor in response to incident photons, the photosensor may integrate or otherwise accumulate the results of the electrical sensing events during a time period referred to herein as a "sensing period" or "sense period".

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described. A central wavelength or frequency or other value indicating a central photon energy of a range or subrange is sometimes referred to herein as a "central energy", and may be obtained in various ways, such as by finding an energy that has maximum intensity or that is another type of central value such as a mean or median of the distribution of light within the range or subrange.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

Some of the photosensing implementations described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing. exposed regions of thin films through a photolithographically patterned resist layer or other patterned layer; techniques for polishing, planarizing, or otherwise modifying exposed surfaces of materials; and so forth.

In general, the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given' software component can often be replaced by an equivalent hardware component without significantly changing operation of circuitry.

Circuitry can be described based on its operation or other characteristics. For example, circuitry that performs control operations is sometimes referred to herein as "control circuitry" and Circuitry that performs processing operations is sometimes referred to herein as "processing circuitry".

An "integrated circuit" or "IC" is a structure with electrical components and connections produced by microfabrication or similar processes. An IC may, for example, be on or over a substrate on which it was produced or another suitable support structure. Other components could be on the same support structure with an IC, such as discrete components produced by other types of processes.

Implementations of ICs described herein include features characterized as "cells" (or "elements") and "arrays", terms that are used with related meanings: An "array" is an arrangement of "cells" or "elements"; unless otherwise indicated by the context, such as for a biological cell, the words "cell" and "element" are used interchangeably herein to mean a cell or an element of an array. An array may also include circuitry that connects to electrical components within the cells such as to select cells or transfer signals to or from cells, and such circuitry is sometimes referred to herein as "array circuitry". In contrast, the term "peripheral circuitry" is used herein to refer to circuitry on the same support surface as an array and connected to its array circuitry but outside the array. The term "external circuitry" is more general, including not only peripheral circuitry but also any other circuitry that is outside a given cell or array.

Some of the implementations below are described in terms of "rows" and "columns", but these terms are interchangeable. Also, rows and columns are described herein as examples of "lines". Within an array, a "line" of cells refers herein to a series of cells through which a line can be drawn without crossing areas of cells that are not in the line. For example, in a two-dimensional array in which cells have uniform areas, a line of cells could be a row, a column, a diagonal, or another type of straight line; more generally, a line of cells could be straight or could include one or more non-straight features, such as curves or angles.

An IC includes a "photosensor array" if the IC includes an array of cells, and at least some of the cells include respective photosensors. A cell that includes a photosensor may also include "cell circuitry", such as circuitry that makes connections with the photosensor, that transfers signals to or from the photosensor, or that performs any other operation other than photosensing. In general, a cell's photosensor and cell circuitry are within a bounded area of the array, an area sometimes referred to herein as the "cell's area". The part of a cell's area in which an incident photon can be photosensed is referred to herein as "sensing area".

In an application of an IC that includes a photosensor array, circuitry that "responds to" one or more photosensors can be any circuitry that, in operation, receives information from the photosensors about their photosensing results through an electrical connection. Circuitry that responds to a photosensor could be circuitry in the same cell as the photosensor, or it could be array circuitry, peripheral circuitry, or other external circuitry, or it could include any suitable combination of cell circuitry, array circuitry, peripheral circuitry, and other external circuitry. Circuitry that responds to a photosensor could employ any suitable technique to readout photosensing results, including, for example, CCD, CMOS, or photodetector array (PDA) techniques.

An IC is or includes a "position-sensitive detector" or "PSD" if it includes a substantially continuous photosensitive surface and it provides electrical signals indicating a position resulting from a pattern of incident light on the photosensitive surface. For example, the signals could be two currents whose normalized difference is proportional to a centroid of the incident light pattern.

FIG. 1 illustrates general features of product 10, an example of an implantable product that can be implemented as described in greater detail below. As with other implementations described below, product 10 involves a combination of parts or components. For example, product 10 includes parts 12 and 14, which could be referred to herein as first and second parts or as analyte and reference parts. In the illustrated implementation, parts 12 and 14 are connected along dashed line 16, which can be the result of being fabricated together. Product 10 is illustratively long and narrow, resembling a short needle, and FIG. 1 shows one end of product 10.

In the implementations described below, structures, systems, or parts or components of structures or systems may sometimes be referred to as "attached" to each other or to other structures, systems, parts, or components or visa versa, and operations are performed that "attach" structures, systems, or parts or components of structures or systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also making other types of connections such as electrical connections between or among devices or components of circuitry. A combination of one or more parts connected in any way is sometimes referred to herein as a "structure".

Part 12 includes analyte container 20 and part 14 includes reference container 22. Containers 20 and 22 are separated by wall-like structure 24, and container 22 is fully enclosed, with wall-like structure 26 at its side opposite wall-like structure 24 and with each end closed by a similar wall-like structure, with wall-like structure 27 being visible. Container 20, on the other hand, is open, so that bodily fluid 28 can enter and exit, such as through an open end as shown or through openings (not shown) in side wall 29 opposite wall-like structure 24. In general, bodily fluid 28 can be continuously exchanged with surrounding regions to allow for continuous monitoring.

Parts 12 and 14 are each light transmissive, receiving input light through an entry surface as indicated by arrows 30 and providing output light through an exit surface as indicated by arrows 32. The designation of surfaces as entry and exit surfaces can, however, be somewhat arbitrary, and it may be possible in some implementations to reverse direction of input and output light, to have multiple entry or exit surfaces, or to both receive input light through and provide output light at the same surface; the term "light interface surface" is therefore used herein as a generic term that includes any of these types of entry and exit surfaces.

Partial structure 34, which can be implemented with glass or other light-transmissive material, includes light reflective component 36, while partial structure 40, also light-transmissive, similarly includes light reflective component 42. As a result, each of parts 12 and 14 has a respective optical cavity between light-reflective components 36 and 42. As suggested in FIG. 1, light interface surfaces of the first and second parts 12 and 14 are aligned so that they can receive input light from the same light source (not shown) and can similarly provide output light to the same photosensing component (not shown). This feature would be present whether photosensing output light from transmission modes or reflection modes. In general, light interactive surfaces are "aligned" in a given application with one or both of an external light source and an external photosensing component if they are in approximately the same plane or other surface such that input light from the application's external light source is received similarly on both surfaces and/or output light to the application's photosensing component is provided similarly from both surfaces.

A structure may be described by its operation, such as a "support structure" that can operate as a support as described above; similarly, an "optical cavity structure", such as product 10, includes parts or components that can operate as an optical cavity; other examples are defined below. In addition, a structure may be characterized by the nature of its parts or the way in which they are connected; for example, a "layered structure" is a structure that includes one or more layers, and a "partial structure" refers to a structure that is in turn part of another structure.

The term "reflective optical cavity", or simply "optical cavity" or "cavity", refers herein to a light-transmissive region that is at least partially bounded by light-reflective components, with the light-reflective components and the light-transmissive region having characteristics such that a measurable portion of light within the light-transmissive region is reflected more than once across the light-transmissive region. An "optical cavity component" is a component that includes one or more optical cavities.

Within the broad category of optical cavities, there are various more specific types: For example, a laser cavity, mentioned above, is an example of an "emitting optical cavity" or simply "emitting cavity" that can operate as a source of emitted output light even when it is not receiving input light from an external light source, with the emitted light ordinarily resulting from a gain medium within the light-transmissive region; similarly, a "transmissive cavity" can operate, in response to input light from one or more external light sources at an entry surface, providing a transmitted portion of its output light at an exit surface different than the entry surface (a complementary, reflected portion may be provided at the entry surface); a "Fabry-Perot cavity" is a reflective optical cavity in which constructive interference (or positive reinforcement) occurs in one or more photon energy subranges while destructive interference occurs in others.

A Fabry-Perot cavity or other optical cavity that can operate to provide output light in one or more photon energy subranges while not providing output light with other photon energies may be described as having one or more "modes", each for a respective one of the output light energy subranges; if the cavity is a transmissive cavity, modes of its transmitted output light may be referred to as "transmission modes" and modes of its reflected output light may be referred to as "reflection modes". In the reflection spectrum, either the valley-like dips or the plateau-like reflection bands between the dips can be considered as "reflection modes". An emitting cavity can be described as "stimulated at" a mode by any operation that results in emission of output light in the mode's photon energy subrange. Similarly, a transmissive cavity can be described as "illuminated at" a mode by any operation that provides input light that results in transmission or reflection of output light in the mode's photon energy subrange.

In typical implementations of optical cavities, two light-reflective components have approximately parallel reflection surfaces and the light-transmissive region is sufficiently uniform that measurements would indicate many reflections of light within the light-transmissive region. Such cavities define a directional orientation as follows: Directions in which light could propagate and be reflected many times within the light-transmissive region are referred to herein as "reflection directions", and generally include a range of directions that are approximately perpendicular to both reflection surfaces. Directions that are approximately parallel to both reflection surfaces, on the other hand, are generally referred to herein as "lateral directions". In addition, the terms "in", "inward", or "internal" generally refer to positions, directions, and other items within or toward the light-transmissive region between the reflection surfaces, while "out", "outward", and "external" refer to positions, directions, and other items outside or away from the light-transmissive region. In general, it should be understood that the above directional orientation is arbitrary and only for ease of description, and that an optical cavity may have any appropriate orientation.

The above directional orientation does not in general apply to angle of incidence of input light. Transmissive cavities can typically operate in response to incident light that is not perpendicular to entry surfaces or reflection surfaces. Light incident on a transmissive cavity's entry surface at any angle is reflected multiple times within the cavity, producing transmission modes in accordance with the cavity's geometry. But transmission modes are affected by angle of incidence.

Depending on the type of cavity and the angle of incidence, modes can be blue shifted or red shifted in comparison to perpendicular incidence; if all light enters a cavity at approximately the same angle, performance is affected only by the shifting of modes and modes are not also broadened, but performance is reduced if a cavity receives incident light distributed across a large angular range because transmission mode structure is then averaged over multiple angles.

Analyte is "present in", "positioned in", or simply "in" an optical cavity when the analyte is in all or some part of the cavity's light-transmissive region. An optical cavity provides "analyte-affected output light" if the optical cavity's output light is different in some way when analyte is present in the cavity than when analyte is absent, with the difference being due to the analyte's optical characteristics.

Box 50 at the ends of arrows 32 contains a graph, illustrating that the optical cavities of the first and second parts 12 and 14 each have a set of modes in which they provide output light, with intensity functions of three modes of reference cavity 22 being illustrated by solid-line curve 52 and those of counterpart modes of analyte container 20 being illustrated by dashed-line curve 54. The term "intensity function" refers to a function that relates intensity of output light to another parameter, such as photon energy for an "intensity-energy function" or, in some implementations, position of a light interface surface or a photosensitive surface.

An intensity function can have any of a wide variety of shapes and features, but a shape that frequently arises in transmission modes is the "peak", a shape characterized by a maximum value from which a curve for the function slopes steeply downward. Peaks have various features, including "central value", meaning the value of the other parameter at which the peak's maximum occurs, such as "central energy" for an intensity-energy function; "maximum intensity" or simply "maximum" or "amplitude", meaning the intensity value at the peak's maximum, whether measured as an absolute intensity or relative to another feature, such as a nearby minimum value; "contrast", meaning a value indicating relationship between magnitudes of the peak's maximum intensity and of one or more nearby minima of the transmission intensity function; and "intermediate intensity width", meaning the width of the peak at an intensity somewhere between its maximum and nearby minima, such as a full width half maximum (FWHM). In general, information can be encoded in one of these features in various ways, including those described in copending U.S. Pat. No. 7,545,513 and incorporated herein by reference in its entirety. Once encoded, such information can also be recovered in various ways, including those described in co-pending U.S. Pat. No. 7,502,123 and incorporated herein by reference in its entirety.

In the illustrated example, the reference fluid in reference container 22 has optical characteristics that provide modes with relatively uniform intensity functions for the first, second, and third modes that are illustrated. Analyte in analyte container 20, however, has optical characteristics that cause changes in features of intensity functions of the modes, such as by changing central value, maximum intensity, or intermediate intensity width. Therefore, in curve 54, central values or energies of intensity functions for the first, second, and third modes are illustratively shifted from curve 52, such as by a change in refractive index; similarly, amplitudes and FWHMs of intensity functions of the second and third modes are changed from curve 52 to curve 54, such as by changes in absorption spectrum. Additional details about effects of refractive index and absorption and encoding techniques are provided in co-pending U.S. Pat. No. 7,545,513 and incorporated herein by reference in its entirety.

As a result of these features, product 10 can be used in applications in which optical characteristics of a bodily fluid are compared with those of a reference fluid. Furthermore, as suggested by arrow 28, product 10 can be implanted within the body, allowing bodily fluid to enter and exit from container 20, such as from blood, lymph, or interstitial fluid, and continuous monitoring is possible if fluid is continuously exchanged in this manner.

The general features in FIG. 1 could be implemented in many ways, as exemplified by the various implementations described below. Parts of product 10 could be made of any of a wide variety of materials in various shapes and sizes and using a wide variety of different fabrication techniques. Further, connections between parts 12 and 14 and between other parts could be made in a wide variety of ways using various connecting techniques, including various deposition, coating, bonding, adhesive, or other connecting techniques.

FIG. 1 illustrates an example in which product 10 can be long and narrow, facilitating implantation, and insertion into a human body will also be easier if its transverse outer dimensions do not exceed approximately 0.5 mm. Current thin film fabrication technology can easily produce a structure of this size. Openings into the analyte container can be shaped, sized, and located for the required update time constant and other constraints of the application; for example, for monitoring a homogeneous fluid for glucose, it may be desirable for fluid to enter and exit freely in as many directions as possible, so that wall 29 in FIG. 1 may have many large openings along its length.

Product 10 could be implemented with a wide variety of types of optical cavity techniques. For example, it can operate as a homogeneous optical cavity, and its output light can pass through an LVF or other laterally varying transmission structure before being photosensed, such as by a photosensor array. This technique allows information to be obtained on the optical properties at multiple sampling points per readout. In this approach, product 10 could also be implemented with a tunable cavity, such as with deformable spacers, to set its wavelength range during manufacture or to adjust it during use, to provide a different set of sample points at each position. On the other hand, product 10 could operate as an inhomogeneous cavity illuminated, for example, by multiple narrow band light sources, either in an array or fired in sequence, so that photosensed readout provides sampling points, e.g. for a refractive index and absorption value, for each of the light sources. If implemented as an inhomogeneous cavity similar to an LVF connected to provide its output light to a photosensor array, product 10 can have a cavity thickness suitable to a given number of output light modes; for example, it could be sufficiently thin to transmit only a single mode at each position, in which case it could be illuminated by a broadband light source adjusted to its spectral range. In any case, product 10 could be used in a system that applies referencing techniques to reduce the effects of noise and inhomogeneities, especially adjustment of measurements from the analyte cavity based on measurements from the reference cavity, but also possibly including self-calibration and other. types of referencing as mentioned below.

Figure 2:
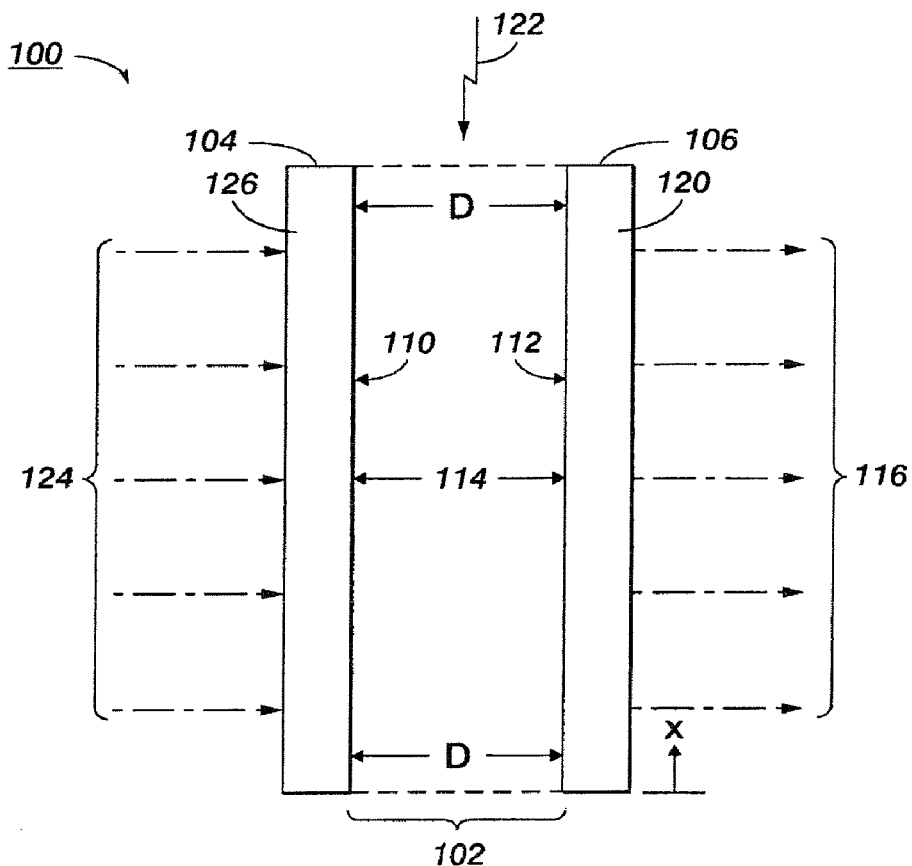
FIG. 2 is a schematic side view of a homogeneous optical cavity that could be used in the product of FIG. 1.

FIG. 2 illustrates optical cavity 100, an example of a "homogeneous optical cavity", meaning a cavity whose light-transmissive region includes an extended part with substantially constant optical distance D between its reflection surfaces, sometimes referred to as its "homogeneous region". The homogeneous region of cavity 100 illustratively includes substantially all of light-transmissive region 102 where it is between and partially bounded by light-reflective components 104 and 106, though partially and completely bounded homogeneous regions with various other shapes and arrangements are possible.

Inward-facing surfaces 110 and 112 of components 104 and 106, respectively, can be implemented, for example, as mirrors or other reflective components that closely approximate the reflection surfaces of cavity 100. The characteristics of components 104 and 106 and of any material or structure within region 102 are such that a measurement would indicate that at least a portion of light within region 102 is reflected more than once. A reflection direction in which light can be repeatedly reflected between the reflection surfaces is represented by bidirectional ray 114, while one of the possible lateral directions in an x-y plane approximately perpendicular to ray 114 is illustrated by an x-axis at the lower right.

FIG. 2 also illustrates two ways in which homogeneous optical cavities can operate to provide output light, represented schematically by arrows 116. In both operations, output light can be provided at an exit surface, illustratively outward-facing surface 120 of component 106, which may or may not be approximately parallel to the reflection surfaces.

In the first operation, optical cavity 100 operates as an emitting cavity, such as a laser cavity. Typically, an emitting cavity operates in response to stimulation of some type, represented schematically in FIG. 2 by stimulation arrow 122. Stimulation arrow 122 could, for example, represent electrical or optical stimulation.

In the second operation, optical cavity 100 operates as a transmissive cavity, such as a Fabry-Perot interferometer. A transmissive cavity operates in response to input light from one or more external light sources, represented in FIG. 2 by illumination arrows 124. Input light can be received at an entry surface, illustratively outward-facing surface 126 of component 104, which also may or may not be approximately parallel to the reflection surfaces. As noted above, a reflected portion of output light can be provided at the entry surface, as described in greater detail below.

Figure 3:
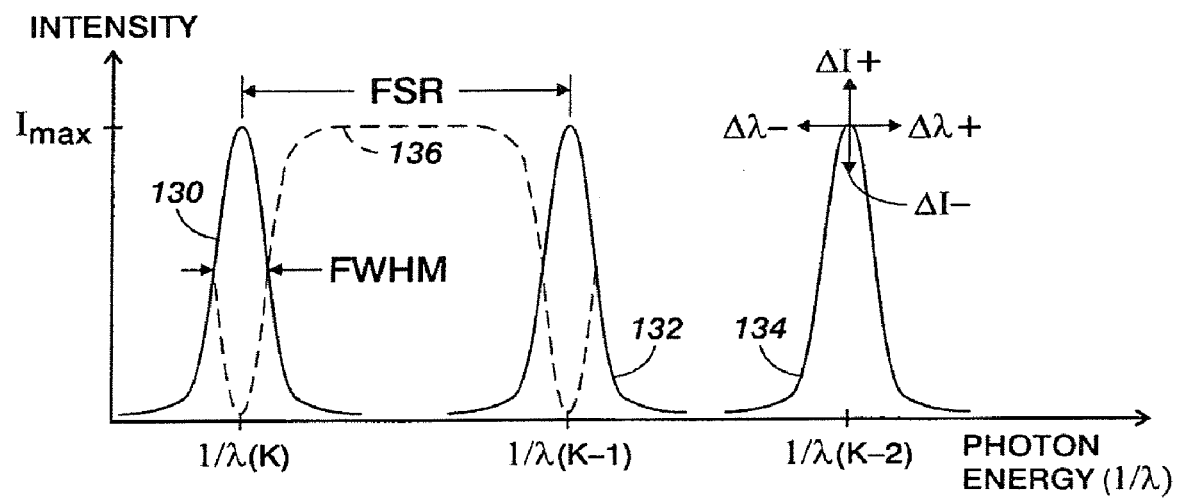
FIG. 3 is a graph showing intensity-energy curves for transmission and reflection from a cavity as in FIG. 2 when operated as a Fabry-Perot cavity, showing ways in which information can be included in transmission mode peaks.

FIG. 3 is an intensity-energy graph or "output spectrum" for optical cavity 100 when operated as a Fabry-Perot cavity such as an interferometer. Since photon energy is inversely proportional to wavelength, wavelength increases as one moves leftward along the horizontal axis, while energy and frequency would increase to the right.

The graph in FIG. 3 includes a solid-line curve with peaks 130, 132, and 134, each of which is an "intensity-energy peak" or simply "intensity peak" that results from a respective transmission mode of cavity 100, illustratively the Kth, (K−1)th, and (K−2)th modes, and has an amplitude Imax, which could result from broadband illumination in the photon energy subranges of all the modes shown; such a curve is sometimes referred to herein as a "transmission spectrum". FIG. 3 also includes part of dashed-line curve 136 that is the complement of the transmission spectrum, i.e. the intensity-energy curve for light that is reflected rather than transmitted by optical cavity 100; such a curve is sometimes referred to herein as a "reflection spectrum" and its reflection modes are broad and separated by narrow valleys rather than being narrow peaks separated by broad valleys like the transmission modes. The term "output modes" is sometimes used herein as a generic term that encompasses transmission modes and reflection modes.

The maxima of intensity-energy peaks 130, 132, and 134 (and the complementary minima between reflection bands) are spaced apart as a function of photon energy (illustratively wavelength), and the difference between the central energy of adjacent transmission mode peaks is referred to as "free spectral range" or "FSR". FSR can be treated as the bandwidth over which adjacent intensity-energy peaks do not overlap, while the full width half maximum (FWHM) of the peaks can be treated as the minimum resolvable bandwidth. FSR, FWHM, and their ratio are all sometimes treated as figures of merit in designing a Fabry-Perot cavity.

The wavelength λ of each intensity-energy peak can be obtained from $\lambda(k)=2nD/k$, where n is the refractive index of the cavity and k is a non-zero integer. Therefore, if refractive index of the cavity changes, λ(k) also changes for a given value of k, so that if a peak's central energy changes, as indicated by Δλ+ and Δλ− for peak 134, the change provides information about refractive index change. Similarly, the intensity of the peaks depends on absorption in the cavity, so that if the intensity of a peak departs from Imax, as indicated by ΔI+ and ΔI− for peak 134, the change provides information about absorption change.

Figure 4:
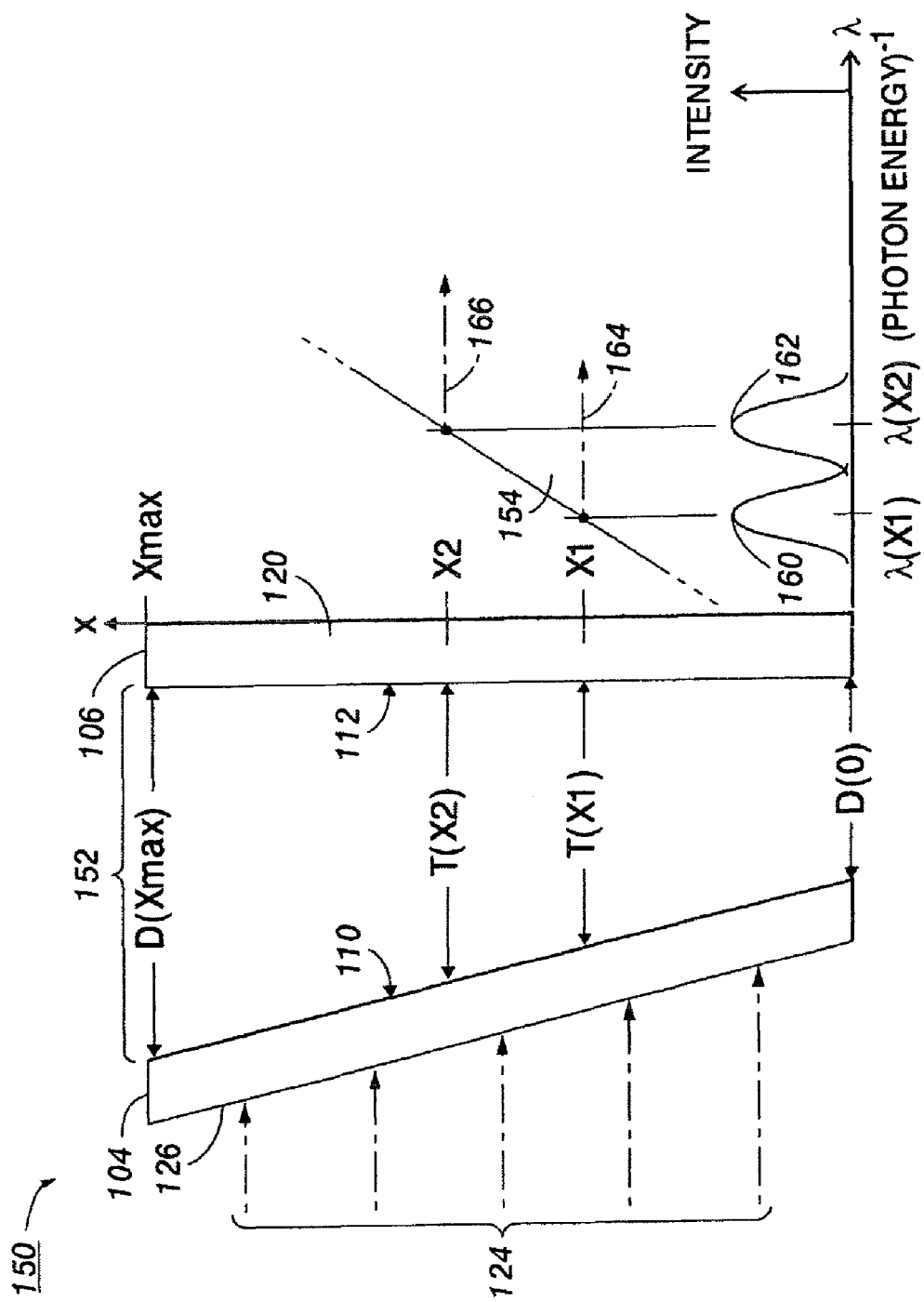
FIG. 4 is a schematic side view of a graded optical cavity that is an example of an inhomogeneous optical cavity that could be used in the product of FIG. 1.

FIG. 4 illustrates graded optical cavity 150, an example of an "inhomogeneous optical cavity", meaning a cavity that does not meet the above definition of a homogeneous optical cavity. Because of the similarities between cavities 150 and 100, parts and components of cavity 150 that are substantially the same as those in FIG. 2 are labeled with the same reference numbers. In cavity 150, however, region 152 is not homogeneous, but rather has "laterally varying optical distance" between reflective surfaces, meaning that the optical distance varies in one or more lateral directions; in the illustrated example, the optical distance illustratively increases linearly from D(0) at one end of cavity 150 (x=0) to D(Xmax) at the opposite end (x=Xmax), but optical distance between reflective surfaces in an inhomogeneous optical cavity could vary laterally in any appropriate way, and need not vary monotonically, linearly, or with any other type of uniformity.

Because of its linearly varying optical distance or thickness, cavity 150 can operate as a linearly variable optical filter (LVF), a type of transmissive cavity. This capability is illustrated by the function T(x), a "laterally varying energy output function" that relates output photon energy (in response to input light represented by illumination arrows 124) to lateral position on exit surface 120. For an LVF, the simple relationship $\lambda(x)=T(x)=d'x+\lambda(0)$ can hold, where d' is a constant that depends on gradient of optical thickness and can be graphically represented by the constant slope $(\lambda(X2)-\lambda(X1))/(X2-X1)$ of position-wavelength graph 154 at right in FIG. 4.

In general, the characteristics of output light at each position on surface 120 can be a function of parameters other than optical thickness, including, for example, photon energy and incident direction of input light 124 received at counterpart positions on surface 126. In particular, the output light may depend on whether the input light is narrow band, broad band, or multi-modal, as can result from a set of transmission or reflection modes. Narrow band or multi-modal illumination of an LVF, for example, can produce one or several output light spots, respectively.

The graphs at right in FIG. 4 also illustrate intensity-energy peaks 160 and 162 that would result if cavity 150 were illuminated by narrow band input light with central energy of λ(X1) and λ(X2), respectively, and, in response, operated as an LVF as described above. At position X1, for example, T(X1) results in transmission of output light represented by arrow 164, within a photon energy subrange characterized by central energy λ(X1); at position X2, T(X2) results in transmission of output light represented by arrow 166, within a photon energy subrange characterized by central energy λ(X2); for the illustrated laterally varying energy output function, if X1≠X2 and the difference between X2 and X1 is sufficient, then T(X1)≠T(X2), and λ(X1)≠λ(X2). On the other hand, for relatively small regions of output surface 120, cavity 150 might in some cases operate locally as a homogeneous cavity with transmission modes as illustrated in FIG. 3: It follows that parameters applicable to transmission modes are sometimes also useful for intensity-energy peaks from inhomogeneous cavities; in particular, information about changes in refractive index and absorption can sometimes be provided through changes in intensity-energy peaks in ways shown in FIG. 3.

Various techniques can be used to produce laterally varying energy distributions with inhomogeneous optical cavities having laterally varying optical thicknesses and, even with homogeneous optical cavities, with angled illumination from a point light source rather than perpendicular illumination; several techniques are described in co-pending U.S. patent application Ser. No. 11/316,438, entitled "Photosensing Throughout Energy Range and in Subranges" and incorporated herein by reference in its entirety. More generally, an inhomogeneous optical cavity can have any appropriate laterally varying energy output function, including functions that are nonlinear or nonuniform in other ways. Some of the below-described implementations, for example, involve functions that are affected by presence of an analyte in an optical cavity. As with homogeneous cavities, an inhomogeneous cavity's light-transmissive region can be completely between and partially bounded by light-reflective components as in FIG. 4, but partially and completely bounded light-transmissive regions with various other shapes and arrangements are possible.

Figure 5:
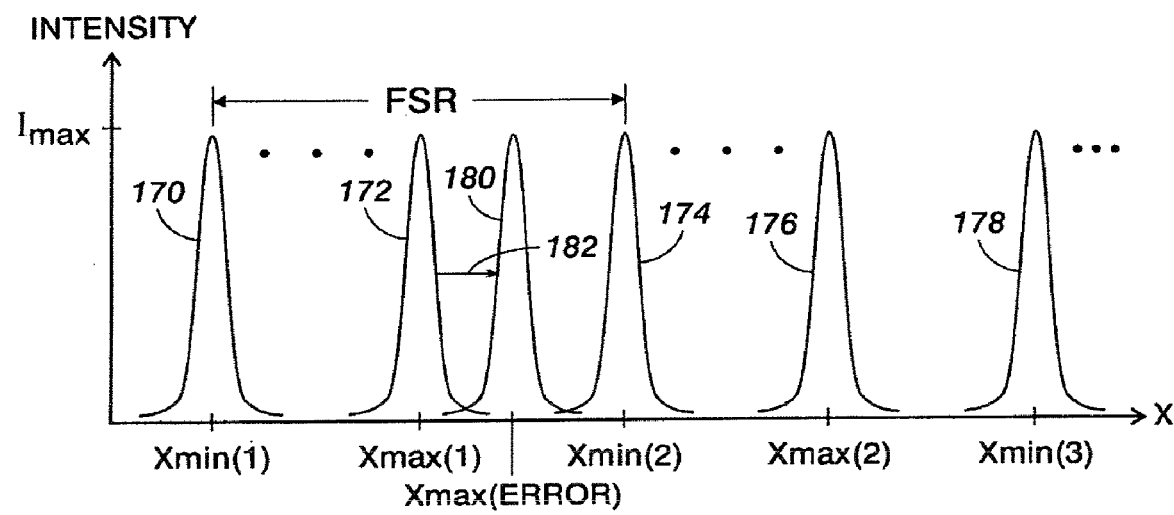
FIG. 5 is a graph showing an intensity-position function of a cavity as in FIG. 4, showing both spectral and harmonic relationships between peaks.

FIG. 5 is an intensity-position graph for optical cavity 150 when operated as a Fabry-Perot cavity such as an interferometer. FIG. 5 is similar to FIG. 3, and the peaks illustratively have maximum amplitude Imax as in FIG. 3 and their central energies and amplitudes (and FWHMs) could be affected as shown for peak 134 in FIG. 3; but the x-axis in FIG. 5 represents position in the x-direction in FIG. 4 rather than photon energy.

In the example shown in FIG. 5, cavity 150 is illuminated at P (P≧2) photon energies ranging from λmin to λmax, resulting in a series of output modes (illustratively transmission modes) for each photon energy λ(p) of illumination at those positions on the x-axis where the condition λ(p)=2n*D(x)/k is satisfied for integer values of k. The first transmission mode shown for λmin is peak 170 at x=Xmin(1) and for λmax is peak 172 at x=Xmax(1). The second transmission mode shown for λmin is peak 174 at x=Xmin(2) and for λmax is peak 176 at x=Xmax(2). The third transmission mode shown for λmin is peak 178 at x=Xmin(3), and so forth.

In the example of FIG. 5, transmission modes are sufficiently separated along the x-axis to prevent interference between adjacent transmission modes. As can be seen, Xmin(2) is sufficiently greater than Xmax(1) that peaks 172 and 174 do not interfere, and Xmin(3) is similarly sufficiently greater than Xmax(2) that peaks 176 and 178 do not interfere. If instead the first transmission mode of λmax were peak 180 due to an increase from Xmax(1) to Xmax(error), as indicated by arrow 182, interference between peaks 180 and 174 would begin to occur; as the first transmission mode of λmax increased further, loss of information would occur due to ambiguity between peak 180 and peak 174. Problems of this type can be avoided by coordination of photon energy range with cavity parameters; for example, cavity thickness D can be sufficiently small that only one output mode occurs over the range from λmin to λmax. The free spatial range (FSR) between the modes of a particular wavelength can also be increased by reducing the tilt of the inhomogeneous (graded) cavity.

Figure 6:
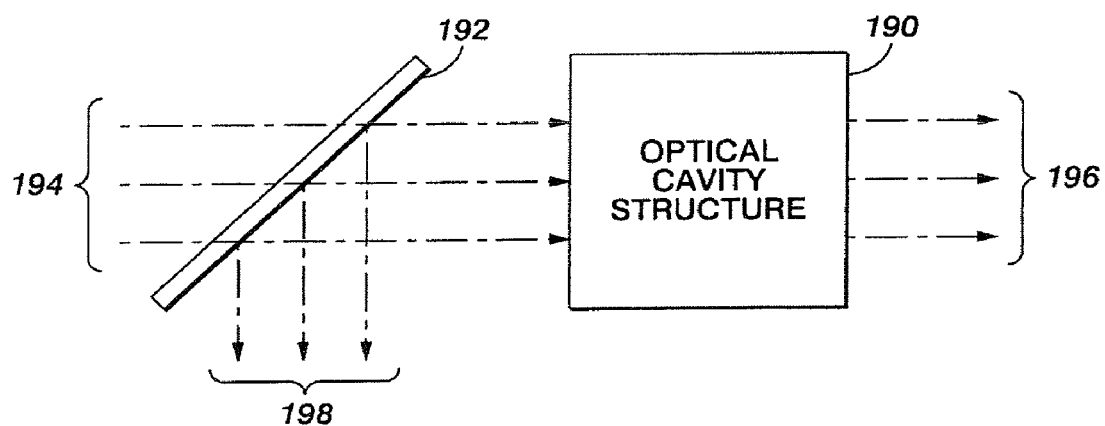
FIG. 6 is a schematic diagram of a setup in which an optical cavity as in FIG. 2 or 4 could operate to provide output light with reflection modes.

FIG. 6 shows a setup in which optical cavity structure 190 receives input light represented by arrows 194 through beam splitter 192. Optical cavity structure 190 can include a transmissive cavity implemented as in any of the ways described in relation to FIGS. 2-5 or in any other suitable way. In response to the input light, the cavity provides a transmitted portion of output light represented by arrows 196 and a reflected portion of output light represented by arrows 198. The use of beam splitter 192 is merely illustrative of ways in which input light and reflected light could be separated; for example, input light could be incident upon an entry surface at a sufficiently large angle from the normal that reflected light is separated from input light, though the non-perpendicular angle of incidence reduces performance of the optical cavity.

As suggested above in relation to FIG. 3, refractive index changes in the optical cavity will cause the same shift in both transmitted and reflected modes, while absorption in the optical cavity will similarly cause decreased amplitude and contrast and increased FWHM in both portions, with the effect of absorption typically varying as a function of photon energy; a curve showing absorption as a function of photon energy is sometimes referred to herein as an "absorption spectrum".

Figure 7:
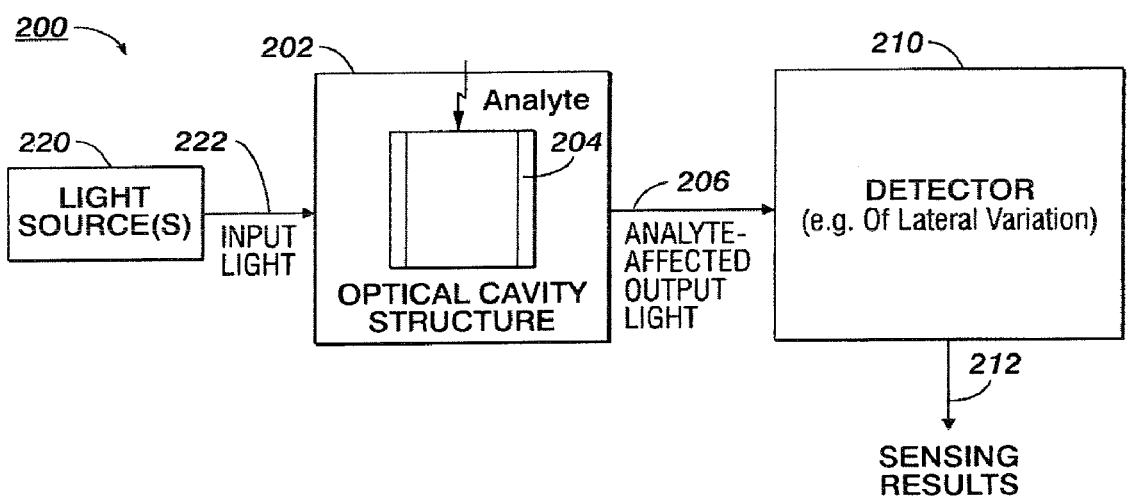
FIG. 7 is a schematic diagram of an implementation of a system that can include an optical cavity structure as in the product of FIG. 1.

FIG. 7 shows system 200, an exemplary implementation of a system that can include an optical cavity structure as in the product of FIG. 1. As used herein, a "system" is a combination of two or more parts or components that can perform an operation together. A system may be characterized by its operation: for example, an "analyte information system" is a system that operates somehow on analyte information; a "processing system" is a system that performs data or signal processing; and so forth.

Within a system, components and parts may be referred to in a similar manner. One component of an analyte information system in which information is obtained about an analyte's optical characteristics, for example, can be a "detector component" or simply "detector", meaning a component that detects light; similarly, a "light source component" includes one or more light sources; an "optical component" performs an optical operation; a "photosensing component" performs a photosensing operation; an "information obtaining component" obtains information, such as from photosensing results; an "adjusting component" performs an adjusting operation, such as on photosensing results; a "light source component" includes one or more light sources; a "light-transmissive component" or simply "transmission component" transmits light; a "light-reflective component" or simply "reflective component" reflects light; and other examples are defined further below. Other parts or components can be characterized by their structure.

System 200 includes optical cavity structure 202, a structure that can include one or more optical cavities with features described above. In system 200, at least one of the optical cavities in structure 202, represented schematically by cavity 204, can contain an analyte, illustratively being provided to cavity 204. The presence of analyte in cavity 204 affects the output light provided by structure 202, and the analyte-affected output light, represented by arrow 206, can then be photosensed within detector 210. For example, detector 210 may include a photosensing component with one or more photosensitive surfaces at which lateral variation of light is detected, such as after the light passes through an LVF. The sensing results from detector 210 can be provided to other components within system 200 or to external components, as represented by arrow 212.

Detector 210 could be implemented in many different ways, such as with a photosensing IC, as described in co-pending U.S. Pat. No. 7,471,399 and incorporated by reference herein in its entirety. The implementation in FIG. 7 might, however, alternatively be implemented with photosensing components that do not include photosensing ICs, such as with one or more discrete photodiodes.

Although cavity 204 can be any suitable type of optical cavity, including an emitting cavity or a transmissive cavity, FIG. 7 illustratively shows one or more light sources 220 that can be included within system 200 to illuminate one or more optical cavities. As represented by arrow 222, structure 202 receives input light from light sources 220. If optical cavity 204 is illuminated as shown, the analyte-affected output light represented by arrow 206 could include one or both of transmitted and reflected light.

Figure 8:
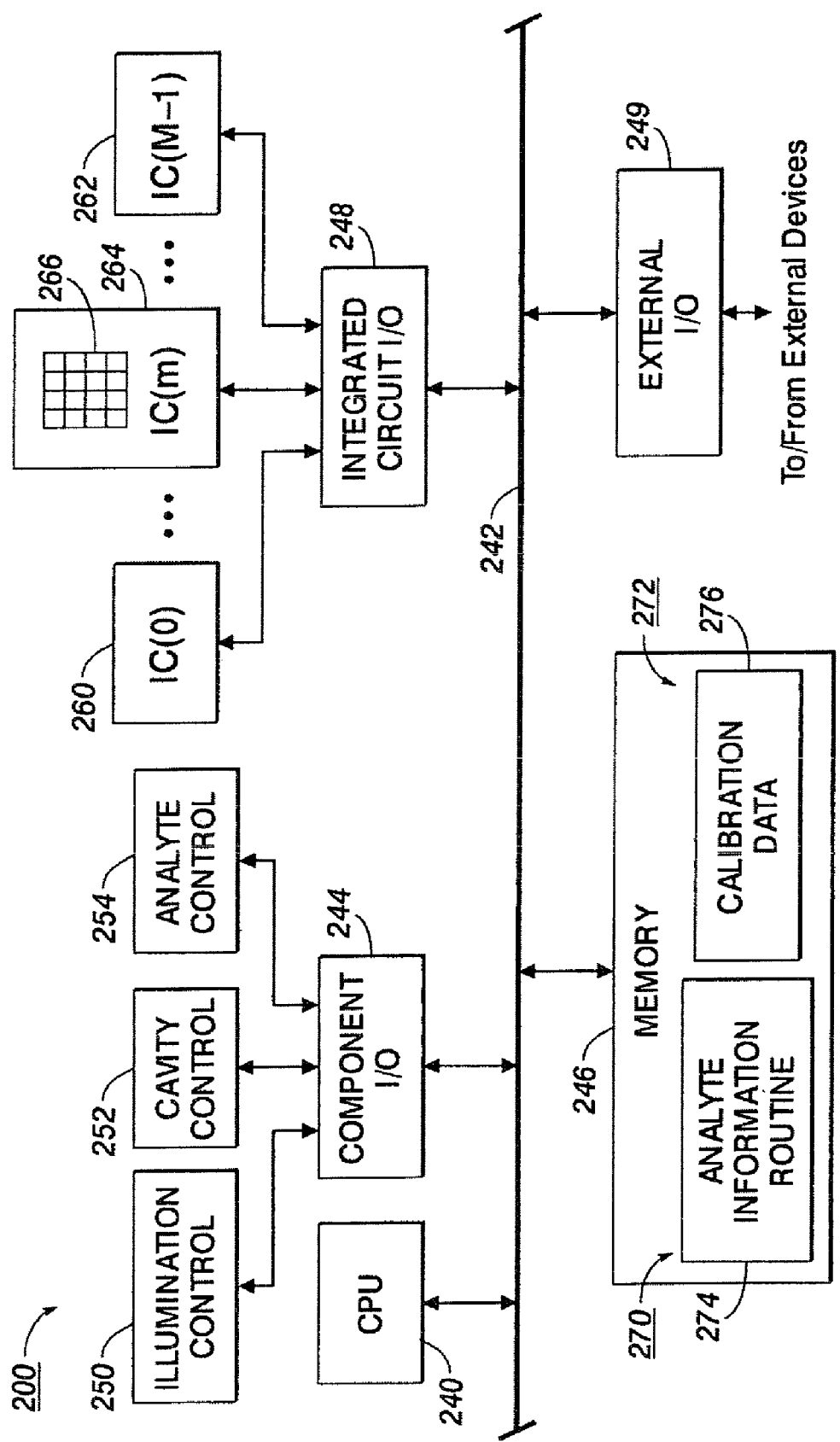
FIG. 8 is a schematic circuit diagram of a system implemented as in FIG. 7.

FIG. 8 illustrates electrical components that can be used in implementing system 200 as in FIG. 7. System 200 illustratively includes central processing unit (CPU) 240 connected to various components through bus 242, but a wide variety of other architectures could be employed, including any appropriate combination of hardware and software, as well as specialized hardware components such as application specific integrated circuits (ASICs) for one or more of the illustrated components or in place of a software component executed by CPU 240.

System 200 also includes component input/output (I/O) component 244, memory 246, integrated circuit input/output (IC I/O) 248, and external I/O 249, all connected to bus 242. System 200 can include various other components (not shown) connected to bus 242. In addition to connections through external I/O 249 by which signals can be provided to and received from external devices, bus 242 can also be connected directly to components outside of system 200.

Component I/O 244 permits CPU 240 to communicate with certain components of system 200, illustratively including illumination control 250, cavity control 252, and analyte control 254. For interactive applications, component I/O 244 could also be connected to a suitable user interface, such as a monitor and keyboard (not shown). In the exemplary implementation in FIG. 7, illumination control 250 can include light sources 220 (FIG. 7) and circuitry for controlling them; cavity control 252 can include electrodes or other components that can be operated to control cavity 204 and other cavities and can also include circuitry connected to those components; and analyte control 254 can similarly include fluidic devices or other components that can operate to transfer analyte into, through, or out of cavity 204 or other cavities or to produce relative movement between analyte and an array or a cavity, and can also include circuitry connected to those devices and components.

In the illustrated implementation of system 200, IC I/O 248 is a similar I/O component that permits CPU 240 to communicate with one or more ICs, such as in detector 210 in FIG. 5. M ICs are illustrated by a series from IC(0) 260 to IC(M−1) 262, including IC(m) 264 with a photosensor array 266.

Memory 246 illustratively includes program memory 270 and data memory 272, although instructions for execution by CPU 240 and data access during execution of instructions could be provided in any suitable way, including through external devices or components. The routines stored in program memory 270 illustratively include analyte information routine 274. In addition, program memory 270 could store various additional routines and also subroutines (not shown) that CPU 240 could call in executing routine 274. Similarly, the data in data memory 272 illustratively include calibration data 276, but could include various additional items of data and data structures accessed by CPU 240.

In executing routine 274, CPU 240 can provide signals to cavity control 252 and to analyte control 254 so that an analyte is present in cavity 204, for example, with the analyte having optical characteristics that affect output light from cavity 204. CPU 240 can also provide signals to illumination control 250 so that cavity 204 is appropriately illuminated to provide analyte-affected output light. CPU 240 can also provide signals to each of ICs 260 through 262 to obtain sensing results that include information about the analyte in cavity 204. In an implementation with a position-sensitive detector (PSD), CPU 240 could instead provide whatever signals are necessary to obtain photosensed quantities from the PSD; for example, CPU 240 could control circuitry to connect output currents from the PSD to a differential amplifier.

Figure 9:
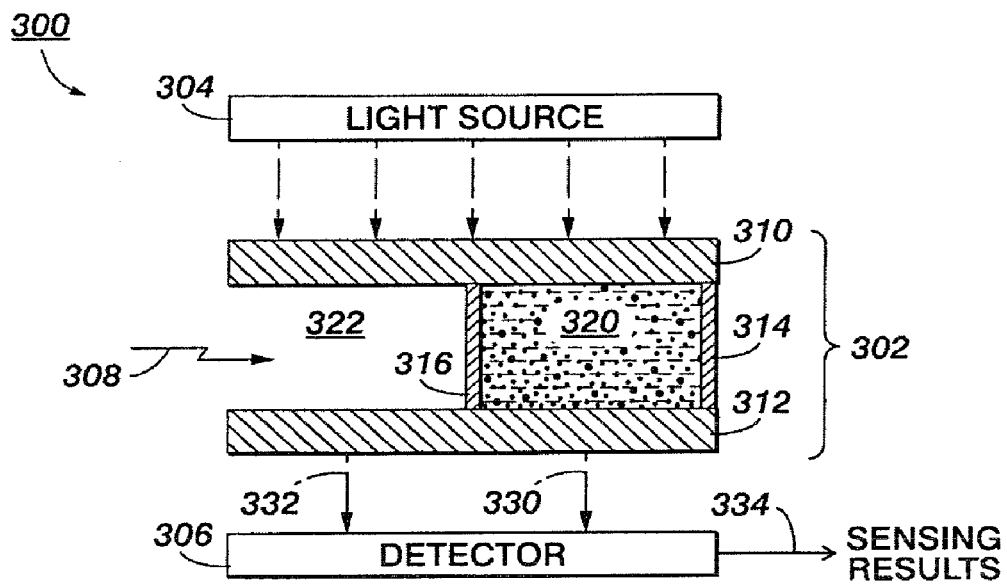
FIG. 9 is a schematic diagram of an implementation of a system as in FIGS. 7 and 8 that can monitor analyte in bodily fluid.

FIG. 9 illustrates application of a system as described above in relation to FIGS. 7 and 8 in which optical cavity structure 202 (FIG. 7) is included in an implantable product with features as described above in relation to FIG. 1, in which case cavity control 252 (FIG. 8) would typically be unnecessary. System 300 illustratively includes optical cavity component 302, light source component 304, and detector component 306, with the implantable product including at least optical cavity component 302, possibly in combination with one or more other components, as described below. Optical cavity component 302 could be an implementation of implantable product 10 in FIG. 1, with the cross section of FIG. 9 taken at a point along the length of product 10 at which wall 29 (FIG. 1) has an opening through which bodily fluid can transfer between the interior and exterior of analyte container 20; in general, an analyte container in an implantable product can be implemented with any suitable combination of one or more such openings, including openings at each end as shown in FIG. 1 and any appropriate number of openings along its length as shown in FIG. 9.

During operation, one or more of the illustrated components of system 300 would be controlled by a processor such as CPU 240 (FIG. 8). In a typical implementation, fluid pressure inside the body could cause movement of bodily fluid containing analyte into an analyte cavity, as indicated by arrow 308, but if power is available in the implantable product for other operations as described below, electrochemical or electromechanical transport processes could also be implemented to manipulate bodily fluid within the analyte cavity, such as to assure representative sampling or to extend the operational life of the implantable product, and such processes could also be controlled by a processor. Power could be available in many possible ways, including, for example, from one or more batteries or, more elegantly and compactly, from one or more photocells or other electromagnetic receivers; an example would be a laser photocell operating with a 630 nm laser diode. The opening into region 322 could be covered, such as by a selective membrane, to allow only certain sizes of analytes to enter and exit.

In operation, optical cavity component 302 receives input light from light source component 304 and, in turn, provides its output light to detector component 306. In the illustrated example, optical cavity component 302 is shown in cross-sectional view, showing how light-reflective components 310 and 312 and wall structures 314 and 316 define two regions between light-reflective components 310 and 312. Region 320, bounded by reflective surfaces of components 310 and 312 and also by surfaces of structures 314 and 316, can contain a reference fluid, while region 322, also bounded by reflective surfaces of components 310 and 312 and also by a surface of structure 316 but open at a side opposite structure 316, can contain fluid that enters as indicated by arrow 308.

In operation, analyte-carrying fluid, such as interstitial fluid from between the cells of a human or other body, can enter region 322 through any appropriate physical process; the analyte can be glucose, for example. As a result, optical cavity component 302 in effect operates as two parallel optical cavities: One optical cavity includes region 320 and provides output light, represented by arrow 330, with information about optical characteristics of the reference fluid; the other optical cavity includes region 322 and provides output light, represented by arrow 332, with information about the analyte. Detector 306 obtains sensing results that include both types of information and the sensing results can be provided to an external component such as a CPU or other processor, as indicated by arrow 334.

Figure 10:
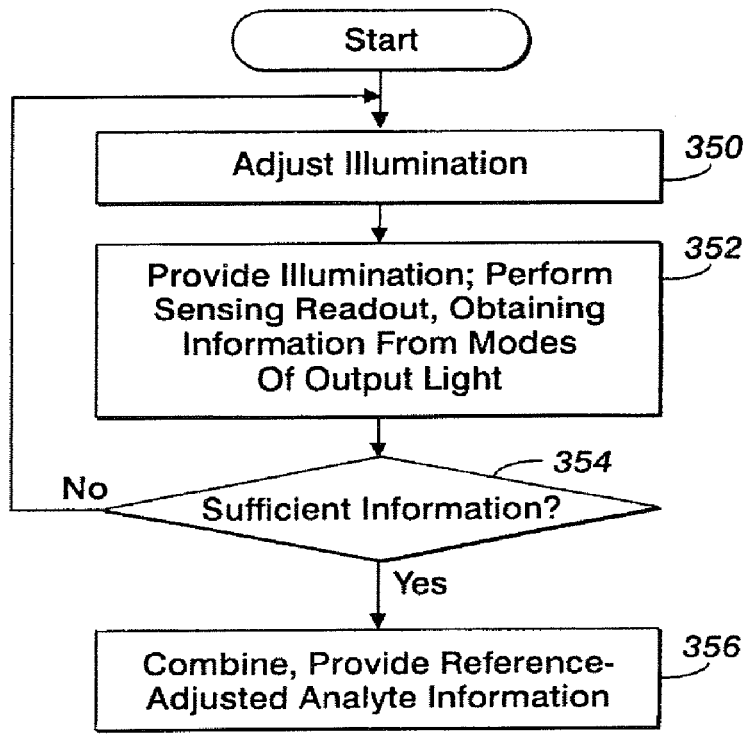
FIG. 10 is a flow diagram showing operations of the analyte information routine in FIG. 8 as it could be implemented in the system of FIG. 9.

FIG. 10 illustrates one example of how analyte information routine 274 (FIG. 8) could be implemented in a system like system 300 in FIG. 9. The routine in FIG. 10 follows a general strategy of iteratively performing a series of one or more illuminate-and-readout operations, each sampling optical characteristics at a discrete sampling point on the photon energy spectrum, until sufficient information about both analyte and reference fluid is obtained, after which reference-adjusted analyte information can be combined and provided. It would also be possible to provide reference-adjusted analyte information after each illuminate-and-readout operation or to provide information both immediately after each illuminate-and-readout operation and also after a series of illuminate-and-readout operations. In either case, the discrete sampling approach is especially suited to a principal component-like analysis.

The operation in box 350 begins each iteration by adjusting the illumination to be provided during the iteration. In this operation, CPU 240 can determine the appropriate illumination for the iteration and can then provide signals to light source 304, such as through illumination control 250 (FIG. 8) to obtain the appropriate illumination.

The operation in box 352 then provides illumination in accordance with the adjustment in box 350 and, concurrently, performs sensing readout during an appropriate sensing period or series of sensing periods. The sensing results obtained from the sensing readout include information from the modes of the output light from both the reference and analyte optical cavities in optical cavity component 302; this information can be encoded, for example, in the ways described above in relation to FIGS. 1, 3, and 5. During this operation, CPU 240 may also provide signals to peripheral circuitry on an IC so that analog quantities photosensed by cells are identified as resulting either from the analyte optical cavity or the reference optical cavity and so that the analog quantities from the analyte are adjusted based on those from the reference. After adjustment, if any, analog quantities can be converted to digital signals for readout. The operation in box 352 can be implemented in whatever manner is appropriate for a given photosensing IC, whether a CCD or CMOS implementation, and regardless of whether readout is purely serial or is also parallel.

If, as described above in relation to FIGS. 1, 3, and 5, information about analyte is encoded in intensity functions of one or more modes, this information can be included in sensing results in various ways. For example, detector component 306 can include a laterally varying transmission structure, so that each mode's reference and analog intensity-energy peaks have respective light spots on a photosensing IC in detector component 306. Therefore, the sensing results can include information about one or both of position, size, and intensity of each light spot and, accordingly, about the respective mode's intensity peaks. If output light from each cavity includes intensity peaks for two or more modes, their respective light spots could be tracked as described in co-pending U.S. Pat. No. 7,502,123 and incorporated herein by reference in its entirety.

The photosensed quantities read out in box 352 can also be digitally adjusted by CPU 240. In other words, information about the reference fluid can be obtained by CPU 240 from the digitized output and can then be used to adjust digitized values obtained for the analyte. For example, the operation in box 352 or a subsequent operation can, for example, make a data manipulation or adjustment to obtain "cavity-only absorption data", an expression that refers herein to values or other data in which information about absorption in an optical cavity is preserved while information is reduced about features exterior to the cavity such as inhomogeneities in illumination and external absorption, as described in co-pending U.S. Pat. No. 7,502,123 and incorporated herein by reference in its entirety. As will be understood, the encoding of absorption information in this manner allows removal of noise-like effects other than those from absorption coefficient inside the optical cavity, influences such as external perturbations, disturbances, or inhomogeneities. As a result, measurements of absorption can have a higher signal to noise ratio. Also, information can be recovered from analyte-encoded output light that is selectively sensitive to absorption changes inside the cavity.

If cavity-only absorption data, such as contrast values, are obtained both for the analyte and the reference fluid, the analyte's values can be adjusted using the reference fluid's values, such as by taking a difference; this is one example of "self-calibration" as that term is used herein. Self-calibration can be especially useful in removing noise-like effects that arise if light source 304 and/or detector 306 are spaced apart from optical cavity component 302, as would be the case for some of the implementations described below. Where input or output light must pass through bodily tissue and fluids, measurements of absorption are subject to noise, but self-calibration can produce a higher signal to noise ratio.

The operation in box 352 can also include other operations. For example, digital adjustment in box 352 can also include any necessary adjustments due to differences in sensing periods or other factors.

With the results from box 352, the operation in box 354 then branches based on whether sufficient information has been obtained in accordance with any appropriate criterion, such as a number of iterations or a minimum set of illuminations. If the criterion is not met, a further iteration is performed, beginning with box 350 as described above. But if sufficient information has been obtained, CPU 240 can perform the operation in box 356 to provide reference-adjusted analyte information, such as in the form of data for another routine or as output through external I/O 249. As shown, this operation can include combining photosensed quantities obtained in box 352, and can also include any additional adjustments, including reference-based adjustments,' that were not performed in box 352. The operation in box 356 can also included further processing, such as to obtain derivates of an absorption spectrum, which is especially useful in regard to glucose.

In performing the operations in boxes 352 and 356, CPU 240 can employ data structures (not shown) stored in memory 246 (FIG. 8). For example, the reference-adjusted analyte information from each iteration could be stored together with previously obtained information in a readout data structure. The operation in box 352 could update the readout data structure before completing each iteration, and then the readout data structure could be provided as output in box 356. If, for example, the operation in box 352 obtains absorption values for the analyte, the readout data structure could provide an absorption spectrum; similarly, refractive index dispersion could be obtained and provided.

The technique in FIG. 10 can also be combined with other types of measurements, such as Raman spectroscopy, intrinsic fluorescence spectroscopy and measurement of fluorescence lifetime, polarimetry to obtain rotation, and so forth, which could be performed using the same implantable product with additional iterations similar to those described above; combining absorption spectrum measurement with orthogonal methods such as polarimetry can improve sensitivity and specificity. The operation in box 356 can be extended to perform multiple signal analysis, and might obtain information about presence of a specific analyte such as glucose.

FIGS. 11-15 illustrate features of several exemplary implementations of system 300 (FIG. 9). In general, however, system 300 could be implemented in many different ways, and can include various implantable products that include optical cavity structures of various kinds, various types and combinations of light sources, and various types of detectors in addition to the examples described below.

Figure 11:
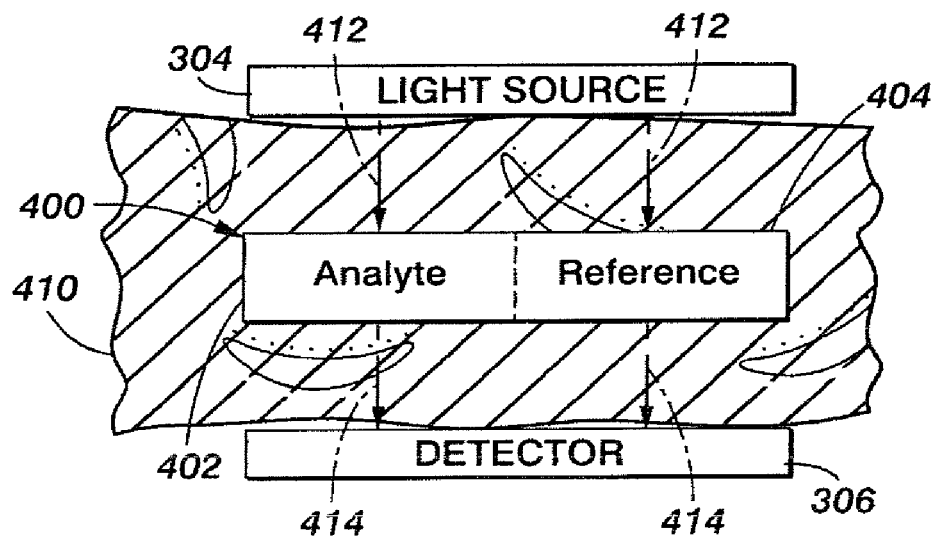
FIG. 11 is a schematic diagram of components in an implementation of the system of FIG. 9.

FIG. 11 illustrates a configuration in which implantable product 400 includes neither light source component 304 nor detector component 306, but does include analyte optical cavity 402 and reference optical cavity 404. As shown, product 400 has been implanted in body part 410, which could be human dermis, and can be illuminated by light source component 304 on or near an exterior surface of body part 410, providing input light represented by arrows 412. In response to appropriate illumination, optical cavities 402 and 404 operate to provide output light represented by arrows 414. Detector component 306, also on or near an exterior surface of body part 410, photosenses the output light, providing sensing results as described above.

The configuration in FIG. 11 may be especially appropriate if input and output light are in the wavelength ranges 600-1100 nm or 2.1-2.5 µm, in which absorption by water and tissue allows a transmission window in which it may be possible to measure absorption of certain important analytes such as glucose. If implemented as a completely passive optical unit, product 400 may not require any electrical power. The configuration in FIG. 11 may, however, involve issues of orientation of components to ensure that illumination and detection are efficiently performed.

Orientation of components can result in non-perpendicular incidence of input light on optical cavities. Unless all output light is incident on one position of the detector component or the detector component has only a single large area as with some PSDs, adjustments can be made to correct for non-perpendicular incidence of input light: For example, if the light source component emits light from a point source at many different angles that are accordingly transmitted through the cavities at various angles, the detector component's photosensitive surface receives the output light at many different angles, but each cell of a photosensor array would receive only a very small angular distribution; therefore, if the angle could be known, as would be the case in a fixed geometry but may not be the case in FIG. 11, the angle-induced variation can be easily corrected.

Figure 12:
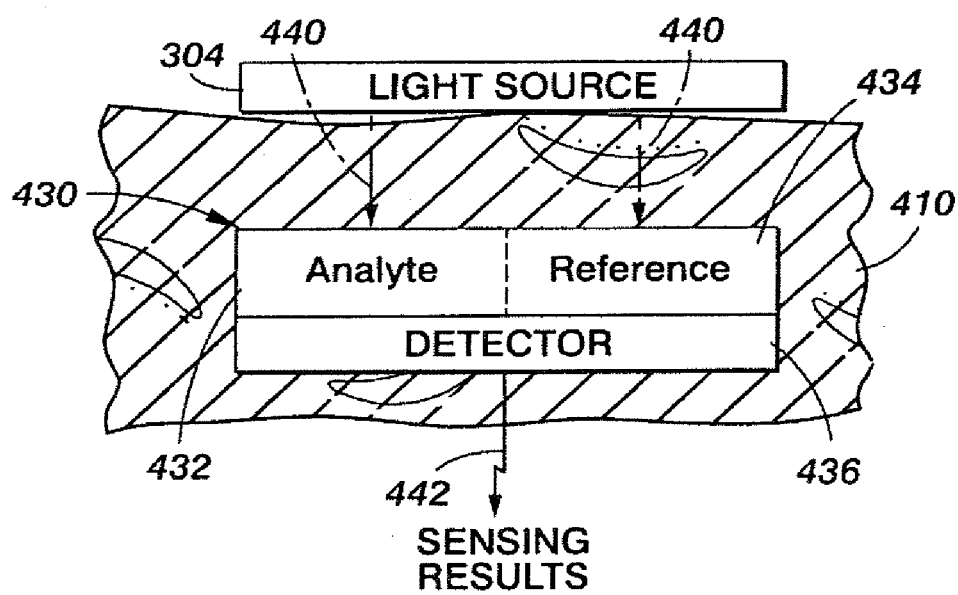
FIG. 12 is a schematic diagram of components in another implementation of the system of FIG. 9.

FIG. 12 illustrates a configuration in which implantable product 430 does not include light source component 304, but does include analyte optical cavity 432, reference optical cavity 434 and detector component 436. As shown, product 430 has again been implanted in body part 410, and, as in FIG. 11, can be illuminated by light source component 304 on or near an exterior surface of body part 410, providing input light represented by arrows 440. In response to appropriate illumination, optical cavities 432 and 434 operate to provide output light to detector component 436, connected to optical cavities 432 and 434 in any appropriate way. Detector component 436 photosenses the output light and provides sensing results, such as by transmitting electromagnetic or other signals represented by arrow 442.

The configuration in FIG. 12 may also be appropriate if input and output light are in the wavelength ranges 600-1100 nm or 2.1-2.5 µm, for the same reasons as FIG. 11. In this configuration, product 430 must have an electrical power source for detector component 436. It may also involve issues of orientation of components to ensure that illumination is efficiently performed. If the measurements are referenced to a reference medium many of the issues with regard to the misalignment of the components can be corrected, since analyte and reference measurement are affected in the same manner.

Figures 13, 14:
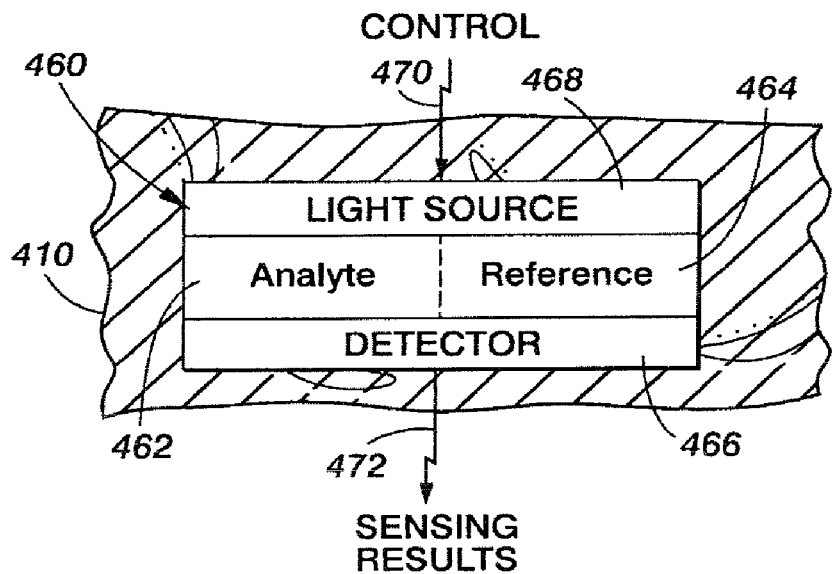
FIG. 13 is a schematic diagram of components in yet another implementation of the system of FIG. 9.
FIG. 14 is a schematic side view of a graded optical cavity that can contain analyte and reference fluid and could be used to implement an implantable product as in FIGS. 1, 9, and 11-13.

FIG. 13 illustrates a configuration in which implantable product 460 includes analyte optical cavity 462, reference optical cavity 464, detector component 466, and light source component 468. As shown, product 460 has again been implanted in body part 410, but does not require illumination from outside the body as in FIGS. 11 and 12. Instead, light source component 468, connected to optical cavities 462 and 464 in any appropriate way, can illuminate cavities 462 and 464 in response to receiving electromagnetic or other control signals represented by arrow 470. In response to appropriate illumination, optical cavities 462 and 464 operate to provide output light to detector component 466, connected to optical cavities 462 and 464 in any appropriate way. As in FIG. 12, detector component 466 photosenses the output light and provides sensing results, such as by transmitting electromagnetic or other signals represented by arrow 472.

The configuration in FIG. 13 similarly must have an electrical power source for both light source component 468 and detector component 466. It may also involve issues of orientation of components to ensure that illumination is efficiently performed, although these issues are greatly reduced in this case since all components can be fixed relative to each other.

FIG. 14 shows device 500, variations of which can also be used to implement implantable products 400, 430, and 460 in FIGS. 11-13. As shown, device 500 can include an LVF-like inhomogeneous optical cavity, which could be illuminated during operation in any appropriate way, including with multiple narrow band light sources. The cavity could be part of a structure that also includes a photosensing component that photosenses its output light, such as in the ways described in co-pending U.S. Publication No. 2008/0186494 and incorporated herein by reference in its entirety. Device 500 can also be implemented with a tunable optical cavity, as described in co-pending U.S. Pat. No. 7,633,629 and incorporated by reference herein in its entirety.

Light-reflective components 502 and 504 provide reflection surfaces on either side of region 506, which can include two containers, one containing analyte-containing fluid and the other reference fluid, as shown. As a result, when input light, represented by arrows 508, is received through component 502, inhomogeneous optical cavity operation as described in relation to FIGS. 4 and 5 can occur separately for each container, resulting in transmission of output light in one or more modes of each optical cavity to photosensing component 510. The indices of refraction of analyte and reference fluid in their respective parts of region 506 and the positioning of structures 502 and 504 determine positions of light transmission, and illumination in a single narrow wavelength band can be provided so that only one wavelength is transmitted from each optical cavity but at different output light positions for the two cavities due to their different optical characteristics, as suggested by arrows 512.

Figure 15:
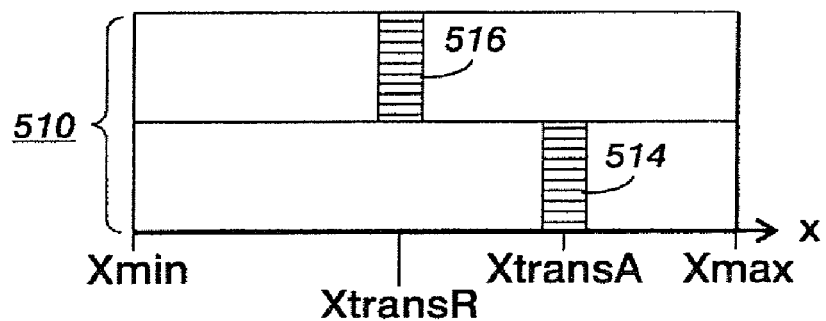
FIG. 15 is a schematic top view of a photosensing component as in FIG. 14.

FIG. 15 shows an example of the pattern of light on the upper surface of photosensing component 510 if the optical cavities were both illuminated in only one narrow wavelength band. As shown, light spot 514 on the analyte cavity side of photosensing component 510 indicates that the incident narrow band light is transmitted at a certain position XtransA from the analyte cavity, but the same narrow band is transmitted from the reference cavity at a different position in the x-direction, displaced from XtransA either toward Xmin (as shown by light spot 516 on the reference cavity side of photosensing component 510 at XtransR) or toward Xmax, depending on the difference between refractive indices of analyte and reference fluids. If analyte absorption changes, causing a change in intensity, contrast, and FWHM of output light's intensity function from the analyte container, the size and intensity of light spot 514 would change relative to light spot 516. In this way, the difference in the intensity functions of the two light spots provides information about the refractive index and absorption of the analyte.

Inhomogeneous optical cavities that contain analyte and reference fluid can be implemented in many ways in addition to the way illustrated in FIGS. 14 and 15. Additional techniques are described in co-pending U.S. No. 2008/0186494 and incorporated herein by reference in its entirety.

Figure 16:
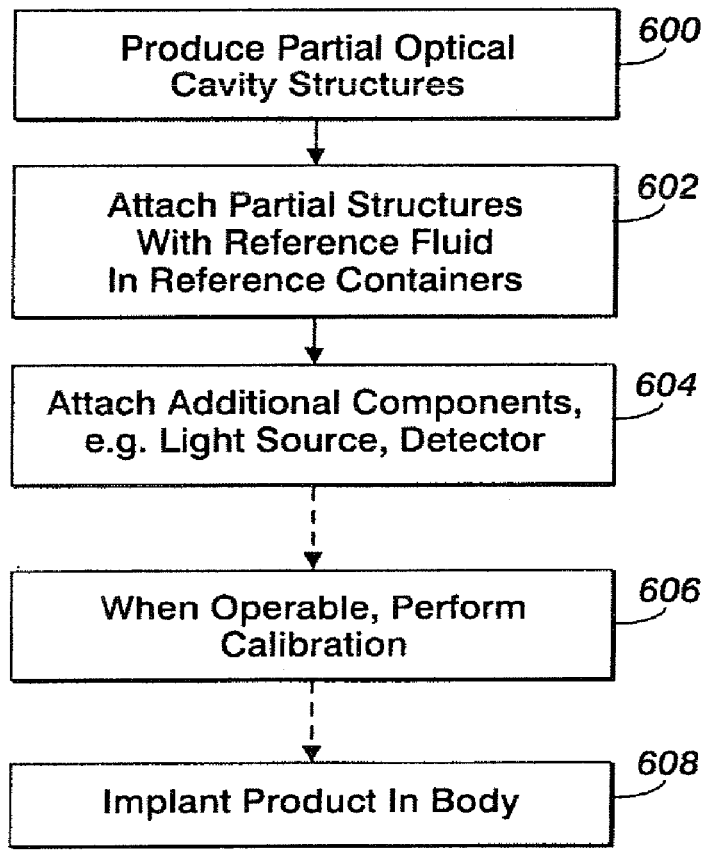
FIG. 16 is a flowchart showing operations in producing and implanting products as in FIGS. 1, 9, and 11-14.

FIG. 16 illustrates exemplary operations in producing products like implantable products 400, 430, and 460 in FIGS. 11-13. In particular, the operations in FIG. 16 make it possible to produce implantable products that include analyte and reference containers, each of which is within a respective optical cavity that can be operated to provide output light in one or more modes with information about optical characteristics of analyte and reference fluid.

The operation in box 600 in FIG. 16 produces two partial optical cavity structures. This operation can include producing a light reflective structure on each of two substrates, similar to light reflective structures 36 and 42 in FIG. 1. This operation can also include producing a patterned layer of SU-8 or polydimethylsiloxane (PDMS) on one or both of the light-reflective structures, such as with techniques described in co-pending U.S. Pat. No. 7,358,476 and incorporated herein by reference in its entirety. Each patterned layer could include structures such as wall-like structures 24 and 26 in FIG. 1 and wall structures 314 and 316 in FIG. 9, together with other wall-like structures that enclose the reference container and partially enclose the analyte container.

If appropriate, an anti-adhesive coating can be applied to surfaces of the two containers, such as by dip-coating polyethylene glycol (PEG) or by providing a coating of parylene C or vapor deposit tetraglyme; these measures may be helpful in extending the operating life of an implantable product, by preventing clogging. Similarly, the product can include an input filter of a suitable kind in the opening into the analyte container, to minimize background.

The two partial structures can also have appropriate dimensions to satisfy various constraints. For example, for a compact, minimally invasive, disposable product, small dimensions are required. The volume of the resulting analyte cavity, for example, could be as small as a few 100 pi; even with a very small volume, adequate light-analyte interaction can occur in an optical cavity if reflectivity of reflection surfaces is sufficiently high. At the same time, dimensions must be chosen that can produce the desired optical cavity modes over the desired range of photon energies with the available illumination, such as to obtain an absorption spectrum or to measure refractive index dispersion; for example, the number of modes depends on the distance between reflection surfaces bounding the cavity. For implementation with an inhomogeneous cavity the following has to be considered: In these cases "multiple narrow band light sources" are used to define the absorption sampling points not the cavity thickness as in the homogeneous cavity cases. Each light source allows determining one refractive and one absorption value. Therefore for implementation with inhomogeneous cavities, a thin cavity thickness can be chosen, which also allows also for operation in spectral regions with higher background absorption. In an example for glucose monitoring, it might be desirable to use the spectral region between 7 and 11 µm in which glucose shows very characteristic glucose absorption peaks but unfortunately also the water background absorption is much higher than in other interesting spectral regions. For example, in the spectral region around 2.2 µm, the water absorption is lower by about a factor of 200, but glucose has a much lower and less specific absorption.

The operation in box 602 then attaches the two partial structures, with reference fluid in the reference container. This could be implemented in many different ways, including, for example, filling the reference container before attaching the partial structures or, alternatively, attaching the partial structures and then inserting fluid into the reference container, such as through a needle, after which an appropriate operation could be performed to ensure the reference container is sealed. The reference fluid can be any appropriate fluid; for glucose, for example, it could be a reference glucose concentration. The operation in box 602 can include forming a suitable bond between the two partial structures so that they are firmly attached to each other.

The operation in box 604 then attaches any other additional components necessary to complete the product. For example, if the product is implemented as in FIG. 12 or 13, detector 436 or detector 466 must be attached by the operation in box 604. Similarly, if the product is implemented as in FIG. 13, light source 468 must be attached to the product by the operation in box 604. The operation in box 604 can also include any other external electrical, optical, or fluidic connections necessary for operation of the product, or, alternatively, such connections could later be made at the time the product is implanted.

The choice of a detector can be made based on several constraints. For example, if intensity peaks of a small number of modes are photosensed to detect changes in central energy or position, amplitude, contrast, and FWHM, it may be possible to use a respective one-dimensional photosensing array for each optical cavity, with each array including a relatively small number of cells, reducing the electrical power requirement because less power is dissipated in the detector. In general, compactness is promoted by using a photosensing IC, as described in co-pending U.S. Pat. No. 7,471,399 and incorporated by reference herein in its entirety.

The operation in box 606 can be performed at any appropriate time after the product is operable, as suggested by the dashed line from box 604 to box 606, and may not be necessary if self-calibration as described above provides satisfactory results. The operation in box 606 performs calibration, which requires appropriate electrical and optical operations, which may require connections of circuitry. In any case, calibration in box 606 can include obtaining items of data or data structures to be used in obtaining analyte information as described herein, and the data or data structures can be stored in memory 246 as part of calibration data 276 (FIG. 8), or, in appropriate cases, can be embedded in analyte information routine 274 or stored in another appropriate form. In particular, the operation in box 606 can include operations that produce one or more calibration tables or reference curves for the reference fluid, such as under different temperatures or other environmental conditions.

Finally, the operation in box 608 implants the resulting product in a body, such as in a human body, to monitor glucose. If the product is sufficiently small, implantation can be performed simply by pushing the product through the skin into an appropriate part of the body in which the analyte container will be filled with blood, lymph, interstitial fluid, or other bodily fluid.

In general, the operations in any of boxes 600, 602, 604, 606, and 608 can include additional activities. For example, at any appropriate point in production of the product, electrical or optical connections can be made so that signals can be provided as necessary. Similarly, connections can be made at any appropriate time to provide electrical power. Also, it might be possible to precisely tune optical cavity dimensions, such as using techniques as described in co-pending U.S. Pat. Nos. 7,633,629 and 7,817,281, both of which are incorporated by reference herein in their entireties.

The technique of FIG. 16 could be modified in many ways within the scope of the invention. For example, the operations in boxes 600, 602, and 604 could be combined in any appropriate way to facilitate attachment of components in a desired sequence. Furthermore, the technique of FIG. 16 is extremely general, and could be employed to produce a wide variety of different products that can be implanted within a body to obtain reference-adjusted information about analytes in bodily fluids.

The implementations described above could be applied in many ways, but an especially important area of application is in continuous or frequent monitoring of glucose concentration as is needed for diabetes management and reduction of complications. Fast, precise, and constant or even continuous glucose monitoring would help ensure detection of episodes of hyper- and hypoglycemia. Current techniques, such as finger-sticking to obtain a blood sample, have various difficulties that might be overcome with a compact optical device.

The implementations described above are consistent with a compact, minimally invasive, disposable product that could be implanted to allow optical measurement of glucose concentration in a small volume of bodily fluid. Such a product could be designed to last an appropriate length of time before it must be replaced; durations of at least two weeks are believed to be achievable with low power consumption measures. It is also believed possible to produce such products at a sufficiently low cost to make disposable versions feasible.

In using such a product, a defined characterization volume of the bodily fluid would be positioned within an optical cavity paired with a reference optical cavity. This technique offers the possibility of continuous self-calibration with a reference fluid under the same environmental conditions and enhanced sensitivity and specificity, and reducing or eliminating the effect of tissue and skin perturbations on measurements.

As described above, features of intensity peaks of an optical cavity's modes can provide information about several optical characteristics of glucose, including absorption spectrum, refractive index dispersion, either or both of which can be measured at discrete sampling points of the energy spectrum. Precise information, such as about central energy, amplitude, contrast, and FWHM of an intensity peak, can be obtained for each sampling point with a chip-size detector, as described in co-pending U.S. Pat. No. 7,471,399 and incorporated by reference herein in its entirety. The information could be obtained in digital form, allowing data processing, which can obtain information with adequate sensitivity and specificity with improved signal-to-noise ratio. In addition to self-calibration using the reference fluid as mentioned above, photosensed quantities and sensing results could be adjusted in various other ways, such as with contrast-based adjustment, such as by measuring a peak-to-valley ratio to obtain the finesse, which is a measure of absorption for a given Fabry-Perot etalon; other contrast-based adjustment techniques are described in co-pending U.S. Pat. No. 7,502,123 and incorporated herein by reference in its entirety.

With data processing techniques that provide sufficient sensitivity, concurrently obtaining the absorption spectrum and refractive index dispersion in the near infrared range, at wavelengths between approximately 2.1-2.5 μm, may be sufficient to determine glucose concentration, though the techniques described herein could be used in almost any wavelength range suitable for glucose sensing. Refractive index information contains absorption information from other spectral ranges, in accordance with the Kramers-Kronig relation, and therefore can be used as additional information on glucose concentration in a multiple signal analysis. Multiple signal analysis could be extended by measuring in multiple wavelength ranges, especially in spectral bands that provide key information on glucose level. It may be possible to perform additional characterization techniques using the same implantable product, such as optical polarimetry and fluorescence. Information could also be used from electrical techniques such as conductivity or capacitance measurement.

Some of the implementations described above in relation to FIGS. 1-16 are examples of implantable products that include an optical cavity structure with first and second optical cavity parts. Each part can be operable as an optical cavity, and each can include a container. The first part's container has at least one opening through which bodily fluid can transfer between the container's interior and exterior when the product is implanted in a body. The second part's container is closed and contains a reference fluid.

In specific implementations, each part can operate as a Fabry-Perot cavity, and can be homogeneous or inhomogeneous, possibly with both parts being tunable; each part can provide output light in a set of modes. The product can also include a light source positioned to provide light to both parts, and it can include a photosensing component positioned to receive light from both parts. The product can include circuitry that receives sensing results from the photosensing component and uses the sensing results to obtain information about the bodily fluid, which could, for example, be a glucose solution.

Some of the implementations described above in relation to FIGS. 1-16 also illustrate examples of a system that includes an implantable product as described above and processing circuitry that adjusts photosensed quantities from the first part's output light based on photosensed quantities from the second part's output light to obtain information about the bodily fluid in the first part's container.

In specific implementations, the system also includes a light source as described above, providing input light under control of the processing circuitry, such as in a set of modes. The light source component can be included in the product, as can a photosensing component.

Some of the implementations described in relation to FIGS. 1-16 also illustrate examples of a method of making an implantable product as described above. The method can produce each of the parts to include a respective container as described above.

In specific implementations, two partial optical cavity structures can be produced and then connected to form the optical cavity structure. Also, a photosensing component or a light source component can be connected to the optical cavity structure.

Some of the implementations described in relation to FIGS. 1-16 similarly illustrate examples of a method of using an implantable product as described above. The method can implant the product in a body, operate a light source component to provide input light to both parts, and then operate a photosensing component to photosense the output light from both parts.

In specific implementations, such a method can use the sensing results from the second part to adjust sensing results form the first part.

Some of the implementations described above in relation to FIGS. 1-16 also illustrate examples of implantable products that include an optical cavity structure with first and second parts. Each part includes a container as described above and a light-transmissive region that includes at least part of its container, and a set of reflective surfaces that at least partially bound the light-transmissive region so that the part can operate as an optical cavity. Each part also has one or more light interface surfaces at which light can enter and exit. The structure in turn has at least one aligned light interface surface in which one surface from both parts is aligned; in operation, the aligned surface receives input light that enters both parts through the aligned surface, provides output light from both parts through the aligned surface, or both.

In specific implementations, in addition to features described above, each of the parts can have both an interface surface that receives the input light and also an interface surface that provides the output light. The input interface surfaces can be aligned in a first aligned surface and the output interface surfaces in another.

The implementations in FIGS. 1-16 illustrate various applications of techniques as described above, including implantable products that include optical cavity structures with containers for bodily fluids and reference fluids. The products can be implanted in bodies and used to obtain and adjust information about an analyte such as glucose in bodily fluid, such as about its refractive index and absorption coefficient. The techniques could be extended to obtain information about polarization and fluorescence, allowing multiple component analysis.

Techniques that use implantable products to obtain information about analytes, as exemplified by the implementations in FIGS. 1-16, can be applied in various diagnostic and monitoring applications, in which a compact, inexpensive, disposable product would be highly desirable. Information about refractive index and absorption, for example, could be used to identify presence or quantity of glucose or another analyte indicating a disease condition. For example, the techniques could be used to measure absorption coefficient and derivative to detect glucose.

Various of the techniques described above have been successfully implemented or simulated, including the production and operation of a highly sensitive detector that includes a commercially available IC covered with a laterally graded Fabry-Perot cavity filter on a glass slide, and that can detect, for example, wavelength shift. Changes of laser and Fabry-Perot mode intensity peaks to indicate analyte optical characteristics have been simulated.

The exemplary implementations described above allow compact, inexpensive implantable products for use in operations such as measuring glucose and other analytes. In general, the techniques can be implemented using existing sensors and photosensors and existing light sources.

The exemplary implementations described above employ optical cavities with specific parameters and modes, but a wide variety of cavities could be used. Cavities with widths in the range from a few microns to hundreds of microns are feasible, and photon energies ranging from the ultraviolet up to the far infrared could be sampled.

Components of exemplary implementations as described above could have various shapes, dimensions, or other numerical or qualitative characteristics other than those illustrated and described above. For example, optical cavities could have any suitable dimensions.

Some of the above exemplary implementations involve specific materials, such as in optical cavity structures and photosensing components, but the invention could be implemented with a wide variety of materials and with layered structures with various combinations of sublayers. In particular, photosensor arrays for a desired speed, sensitivity and wavelength range could have any suitable material, such as silicon, germanium, indium-gallium-arsenide, gallium arsenide, gallium nitride, or lead sulphide, and could be produced with any appropriate kind of devices, including, for example, photodiodes, avalanche photodiodes, p-i-n diodes, photoconductors, and so forth, with any appropriate technique for sensing and reading out information whether based on CCD, CMOS, or other techniques. Various commercially available detector arrays have pixel densities as high as ten megapixels, and some high density ICs have become relatively inexpensive.

Similarly, optical cavity structures could be fabricated with any appropriate techniques, including thin film technology such as sputtering, e-beam or thermal evaporation with or without plasma assistance, epitaxial growth, MBE, MOCVD, and so forth. To produce Bragg mirrors, appropriate pairs of materials with low absorption coefficients and large difference in refractive indices could be chosen, bearing in mind the photon energies of interest; exemplary materials include $SiO_2/TiO_2$, $SiO_2/Ta_2O_5$, GaAs/AlAs, and GaAs/AlGaAs. Thicknesses of layer in optical cavity structures may vary from 30 nm up to a few hundred nanometers.

Some of the above exemplary implementations could involve particular types of optical cavity structures, such as Bragg mirrors and paired distributed Bragg reflectors separated by a Fabry-Perot cavity, but, more generally, any appropriate optical cavity structure could be used. Various techniques could be used to produce optical cavity structures in addition to those described above.

Some of the above exemplary implementations use specific lasers or other light sources to obtain light with desired characteristics, but various other light source techniques could be used within the scope of the invention. Various propagation components that propagate light between other components could also be employed.

The exemplary implementation in FIGS. 8 and 10 employs a CPU, which could be a microprocessor or any other appropriate component. Furthermore, as noted above, adjustment, combining, and other operations on photosensed quantities could be done either digitally or with analog signals, and could be done either on the same IC as a photosensor array, on other components, or on a combination of the two, with any appropriate combination of software or hardware.

The above exemplary implementations generally involve production and/or use of ICs and other photosensing components, optical cavities, light sources, transmission structures, processing circuitry, and control Circuitry following particular operations, but different operations could be performed, the order of the operations could be modified, and additional operations could be added within the scope of the invention. For example, readout of adjusted or unadjusted photosensed quantities from an IC could be performed serially or in parallel, and could be performed cell-by-cell or in a streaming operation.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:
1. A method, comprising:
  receiving input light into an implantable optical structure, the implantable optical structure comprising a first optical cavity and a second optical cavity, each of the first and second optical cavities including a container disposed between opposing reflectors, the container of the first optical cavity having an opening allowing entry of bodily fluids and the container of the second optical cavity being closed and containing a reference fluid;
  transferring bodily fluid between an exterior and interior of the container of the first optical cavity through the opening;

reflecting light input into the first optical cavity more than once across the container of the first optical cavity;

reflecting light input into the second optical cavity more than once across the container of the second optical cavity;

photosensing output light from the first optical cavity and providing first optical cavity photosensing results; and photosensing output light from the second optical cavity and providing second optical cavity photosensing results.

2. The method of claim 1, further comprising:
using the second optical cavity photosensing results to adjust the first optical cavity photosensing results.

3. The method of claim 1, wherein:
an optical distance between the reflectors of the first optical cavity is substantially constant; and
an optical distance between the reflectors of the second optical cavity is substantially constant.

4. The method of claim 1, wherein:
an optical distance between the reflectors of the first optical cavity varies laterally; and
an optical distance between the reflectors of the second optical cavity varies laterally.

5. The method of claim 1, further comprising optically tuning the reflectors of the first and second optical cavities.

6. The method of claim 1, further comprising providing the input light using an implantable light source.

7. The method of claim 1, further comprising:
receiving the first optical cavity photosensing results and the second optical cavity photosensing results in a processor; and
processing the first optical cavity photosensing results and the second optical cavity photosensing results to obtain information about the bodily fluid.

8. The method of claim 7, further comprising providing the input light to the first optical cavity and the second optical cavity under control of the processor.

9. The method of claim 8, further comprising controlling the input light using the processor so that the output light from each of the first and second optical cavities emerges in a set of one or more modes.

10. The method of claim 1, wherein:
the output light from the first optical cavity comprises a first set of one or more modes; and
the output light from the second optical cavity comprises a second set of one or more modes.

11. The method of claim 1, wherein the reference fluid is a glucose solution.

12. A method, comprising:
receiving input light from a light source through a first light interface surface of an implantable optical structure, the first light interface surface common to a first optical cavity and a second optical cavity, each of the first and second optical cavities having a container disposed between opposing reflectors, the container of the first optical cavity having an opening allowing entry of bodily fluids and the container of the second optical cavity being closed and containing a reference fluid;

transferring bodily fluid between an exterior and interior of the container of the first optical cavity through the opening;

reflecting light received through the first light interface surface multiple times between the opposing reflectors of the first optical cavity and through the container of the first optical cavity;

reflecting light received through the first light interface surface multiple times between the opposing reflectors of the second optical cavity and through the container of the second optical cavity;

emitting output light from the first and second optical cavities through a second light interface surface which is common to the first optical cavity and the second optical cavity.

13. The method of claim 12, further comprising
photosensing the output light emitted from the first optical cavity and providing first optical cavity photosensing results; and
photosensing the output light emitted from the second optical cavity and providing second optical cavity photosensing results.

14. The method of claim 13, wherein the output light varies with lateral position according to photon energy.

15. The method of claim 12, wherein the optical structure is operated as a Fabry-Perot interferometer.

16. The method of claim 12, further comprising passing the output light emitted from the first and second optical cavities through a laterally varying transmission structure.

17. The method of claim 12, wherein emitting output light from the first and second optical cavities comprises emitting output light that varies with lateral position according to photon energy.

18. The method of claim 12, wherein emitting output light from the first and second optical cavities comprises emitting output light from each of the first and second optical cavities in only one output mode.

19. The method of claim 12, wherein emitting output light from the first and second optical cavities comprises emitting output light from each of the first and second optical cavities in multiple transmission modes that are sufficiently laterally separated to prevent interference between adjacent transmission modes.

20. The method of claim 12, further comprising generating the input light.

21. The method of claim 20, wherein generating the input light comprises generating light in one broad frequency band.

22. The method of claim 20, wherein generating the input light comprises generating the input light in multiple narrow frequency bands.

23. The method of claim 20, wherein generating the input light comprises generating the input light in multiple narrow frequency bands using multiple light sources fired in sequence, each of the multiple light sources generating one of the multiple narrow frequency bands.

* * * * *